United States Patent
Kim et al.

(10) Patent No.: US 10,663,469 B2
(45) Date of Patent: May 26, 2020

(54) METHOD FOR USING INFORMATION ON COMPLEX BIOMARKER GROUP TO DIAGNOSE LUNG CANCER IN A SUBJECT AND DIAGNOSTIC KIT AND COMPUTING SYSTEM USING THE SAME

(71) Applicant: BioInfra Inc., Seoul (KR)

(72) Inventors: Chul Woo Kim, Seoul (KR); Yong Dai Kim, Seoul (KR); Yong Sung Shin, Seoul (KR); Eun Hee Yeon, Seoul (KR); Kyung Nam Kang, Seoul (KR); Ho Sang Shin, Seoul (KR); Oh Ran Kwon, Seoul (KR)

(73) Assignee: BioInfra Life Science Inc., Seoul (KR)

(*) Notice: Subject to any disclaimer, the term of this patent is extended or adjusted under 35 U.S.C. 154(b) by 0 days.

(21) Appl. No.: 15/429,255

(22) Filed: Feb. 10, 2017

(65) Prior Publication Data

US 2018/0067118 A1 Mar. 8, 2018

(30) Foreign Application Priority Data

Sep. 2, 2016 (KR) .................. 10-2016-0113444

(51) Int. Cl.
| | |
|---|---|
| *G01N 33/48* | (2006.01) |
| *G01N 33/574* | (2006.01) |
| *G16B 25/00* | (2019.01) |
| *C12Q 1/6886* | (2018.01) |
| *G16B 20/00* | (2019.01) |
| *G16B 40/00* | (2019.01) |
| *G06F 30/20* | (2020.01) |
| *G16H 50/20* | (2018.01) |
| *G06F 111/10* | (2020.01) |
| *G16H 50/50* | (2018.01) |

(52) U.S. Cl.
CPC ..... *G01N 33/57423* (2013.01); *C12Q 1/6886* (2013.01); *G06F 30/20* (2020.01); *G16B 20/00* (2019.02); *G16B 25/00* (2019.02); *G16B 40/00* (2019.02); *C12Q 2600/158* (2013.01); *G06F 2111/10* (2020.01); *G16H 50/20* (2018.01); *G16H 50/50* (2018.01)

(58) Field of Classification Search
None
See application file for complete search history.

(56) References Cited

U.S. PATENT DOCUMENTS

| | | |
|---|---|---|
| 2014/0024553 A1 | 1/2014 | Michalek et al. |
| 2014/0094505 A1 | 4/2014 | Chan et al. |

FOREIGN PATENT DOCUMENTS

| | | |
|---|---|---|
| CN | 103703371 A | 4/2014 |
| KR | 10-2013-0004204 | 1/2013 |
| KR | 1020140024916 | 3/2014 |
| WO | 2016094330 A2 | 6/2016 |

OTHER PUBLICATIONS

Frank, Steven A. Immunology and evolution of infectious disease. Chapter 4 Specificity and Cross-Reactivity. Princeton University Press, 2002.*
Bigbee, William L., et al. "A multiplexed serum biomarker immunoassay panel discriminates clinical lung cancer patients from high-risk individuals found to be cancer-free by CT screening." Journal of thoracic oncology 7.4 (2012): 698-708.
Goryainova, ER, and TI Slepneva. "Methods of binary classification of objects with nominal indices." economic theory Journal of the New Economic Associates(2012): 27-49.
Kaftan, Michael W. Encyclopedia of medical decision making. vol. 1. Sage, 2009.
Changyong, F. E. N. G., et al. "Log-transformation and its implications for data analysis." Shanghai archives of psychiatry 26.2 (2014): 105.
Lee, Hyun Joo, et al. "A novel detection method of non-small cell lung cancer using multiplexed bead-based serum biomarker profiling." The Journal of thoracic and cardiovascular surgery 143.2 (2012): 421-427.
Yarilin A.A. "Immunology" // Russia, "GEOTAR—Media", 2010, p. 271.
Iwahori, Kota, et al. "Serum HE4 as a diagnostic and prognostic marker for lung cancer." Tumor Biology 33.4 (2012): 1141-1149.

* cited by examiner

*Primary Examiner* — Anna Skibinsky
(74) *Attorney, Agent, or Firm* — Husch Blackwell LLP

(57) ABSTRACT

A method for diagnosing lung cancer in a subject by using a complex biomarker group is provided. The method includes steps of: (a) a computing system (1) acquiring a model M by using expression level data by individual biomarkers in the complex biomarker group and then (2) acquiring expression level data by the individual biomarkers measured from a biological specimen of the subject or their processed data $B_k$; and (b) the computing system determining whether lung cancer is detected in the subject by using the acquired data of the subject by referring to the model M; wherein the complex biomarker group includes CEA, HE4, ApoA2, TTR, sVCAM-1 and RANTES.

4 Claims, 11 Drawing Sheets

METHOD FOR USING INFORMATION ON COMPLEX BIOMARKER GROUP TO DIAGNOSE LUNG CANCER IN A SUBJECT AND DIAGNOSTIC KIT AND COMPUTING SYSTEM USING THE SAME

CROSS REFERENCE TO RELATED APPLICATION

This application claims priority to and incorporates herein by reference all disclosure in Korean patent application no. 10-2016-0113444 filed Sep. 2, 2016.

FIELD OF THE INVENTION

The present invention relates to a method for using complex biomarker group to diagnose lung cancer in a subject and a diagnostic kit and a computing system using the same, wherein the biomarkers include CEA, HE4, ApoA2, TTR, sVCAM-1 and RANTES.

BACKGROUND OF THE INVENTION

Lung cancer is a cancer that starts in the lung. More than 1.3 million people die every year due to lung cancer. The primary causes of lung cancer are smoking, radon gas, asbestos, genetics, etc. and smoking is known as the biggest cause of lung cancer.

More specifically, lung cancer is classified into small cell lung cancer (SCLC) and non-small cell lung cancer (NSCLC). The NSCLC is the most common cancer that accounts for approximately 80% of all lung cancer cases and it is divided into adenocarcinoma, squamous cell carcinoma, and large cell carcinoma. Because there are differences in histological characteristics as well as prognoses and treatments depending on types of lung cancer, an accurate diagnosis is important. In case of NSCLC, despite the recent development of cancer treatments, the 10-year survival rate for lung cancer is less than 10%, which is very low. This is because it is difficult to diagnose lung cancer in most of patients even with seriously advanced NSCLC.

Typically, early lung cancer does not have any symptoms at all and even after it progresses to some degree, it just has simple symptoms such as cough and expectoration, which are just similar to common cold. Therefore, it is very difficult to diagnose through common medical examinations by interviews, and patients with lung cancer have different symptoms depending on a location where the lung cancer starts. The common symptoms of lung cancer include coughing, blood expectoration or coughing up blood, shortness of breath, chest pain, husky voice, superior vena cava syndrome, bone pain, fracture, headache, nausea and vomiting, but at the time when patients themselves start to recognize such symptoms, the lung cancer may have already progressed to an advanced stage.

Accordingly, at the present time, early detection of lung cancer is the best way to increase survivability of patients.

The best way to detect lung cancer earlier is periodic medical examinations. Upon such medical examinations, whether patients have lung cancer or not can be determined by collecting biospecimens derived from their bodies, such as their blood and urine. As such, an indicator that can be used to identify any change in a body by using protein, nucleic acid, metabolite, etc., included in a biospecimen refers to a biomarker.

For example, according to the conventional biomarker techniques such as Korean Patent Registration No. 10-1463588, it is disclosed that biomarkers consisting of AIAT, IGF-1, RANTES, and TTR are used to diagnose lung cancer earlier. If it is possible diagnose lung cancer with better classification ability than the conventional ones, it may be favorable from the aspects of the time, costs and effects of confirming lung cancer.

SUMMARY OF THE INVENTION

It is an object of the present invention to propose a method for using complex biomarker group to diagnose lung cancer in a subject, and a diagnostic kit and a computing system using the same, wherein the biomarkers include CEA, HE4, ApoA2, TTR, sVCAM-1 and RANTES.

In accordance with one aspect of the present invention, there is provided a method for diagnosing lung cancer in a subject by using a complex biomarker group, including steps of: (a) a computing system (1) acquiring a model M for diagnosing lung cancer, wherein the model M is established by using (i) expression level data by individual biomarkers in the complex biomarker group measured from biological specimens of a sample consisting of lung cancer patients and people without lung cancer or their processed data $B_{ki}$ where k is an index for the individual biomarkers and i is an index for the individual biological specimens of the sample or (ii) the expression level data by the individual biomarkers or their processed data $B_{ki}$ and ages $age_i$ of the sample and then (2) acquiring expression level data by the individual biomarkers measured from a biological specimen of the subject or their processed data $B_k$, or the expression level data by the individual biomarkers or their processed data $B_k$ and ages age of the subject; and (b) the computing system determining whether lung cancer is detected in the subject by using the acquired data of the subject by referring to the model M; wherein the complex biomarker group includes CEA, HE4, ApoA2, TTR, sVCAM-1 and RANTES.

In accordance with another aspect of the present invention, there is provided a lung cancer diagnostic kit for diagnosing lung cancer in a subject by using a complex biomarker group, including: antibodies specifically binding to a carcinoembryonic antigen (CEA), human epididymis protein 4 (HE4), apolipoprotein A-II (ApoA2), transthyretin (TTR), soluble vascular cell adhesion molecule-1 (sVCAM-1), and RANTES {regulated on activation, normal T cell expressed and secreted; Chemokine (C-C motif) ligand 5} as individual biomarkers in the complex biomarker group.

In accordance with still another aspect of the present invention, there is provided a lung cancer diagnostic kit for diagnosing lung cancer in a subject by using a complex biomarker group, including: at least six receptor sites; and six or more antibodies corresponding to biomarkers that are placed on at least six receptor sites respectively and are specifically binding to individual biomarkers in the complex biomarker group; wherein the six or more antibodies include antibodies specifically binding to the individual biomarkers CEA, HE4, ApoA2, TTR, sVCAM-1 and RANTES, respectively, and the lung cancer diagnostic kit is used to determine whether lung cancer is detected in the subject by referring to a model M for diagnosing lung cancer acquired by (1) using (i) expression level data by the individual biomarkers measured from biological specimens of a sample consisting of lung cancer patients and people without lung cancer or their processed data $B_{ki}$ where k is an index for the individual biomarkers and i is an index for the individual biological specimens of the sample or (ii) the expression level data by the individual biomarkers or their processed data $B_{ki}$ and ages $age_i$ of the sample by (2) inputting, in the model M, expression level data by the individual biomarkers measured from a biological specimen of the subject or their processed data $B_k$, or the expression level data by the individual biomarkers or their processed data $B_k$ and ages age of the subject.

In accordance with still yet another aspect of the present invention, there is provided a computing system for diagnosing lung cancer by using a complex biomarker group, including: (a) a communication part for (1) acquiring a model M for diagnosing lung cancer, wherein the model M is constructed by using (i) expression level data by individual biomarkers in the complex biomarker group measured from biological specimens of a sample consisting of lung cancer patients and people without lung cancer or their processed data $B_{ki}$ where k is an index for the individual biomarkers and i is an index for the individual biological specimens of the sample or (ii) the expression level data by the individual biomarkers or their processed data $B_{ki}$ and ages $age_i$ of the sample and then (2) acquiring expression level data by the individual biomarkers measured from a biological specimen of the subject or their processed data $B_k$, or the expression level data by the individual biomarkers or their processed data $B_k$ and ages age of the subject; and (b) a processor for determining whether lung cancer is detected in the subject by using the acquired data of the subject by referring to the model M; wherein the complex biomarker group for diagnosing lung cancer includes individual biomarkers CEA, HE4, ApoA2, TTR, sVCAM-1 and RANTES.

BRIEF DESCRIPTION OF THE DRAWINGS

The following drawings to be used to explain example embodiments of the present invention are only part of example embodiments of the present invention and other drawings can be obtained based on the drawings by those skilled in the art of the present invention without inventive work.

DETAILED DESCRIPTION OF THE PREFERRED EMBODIMENTS

Figure 1:
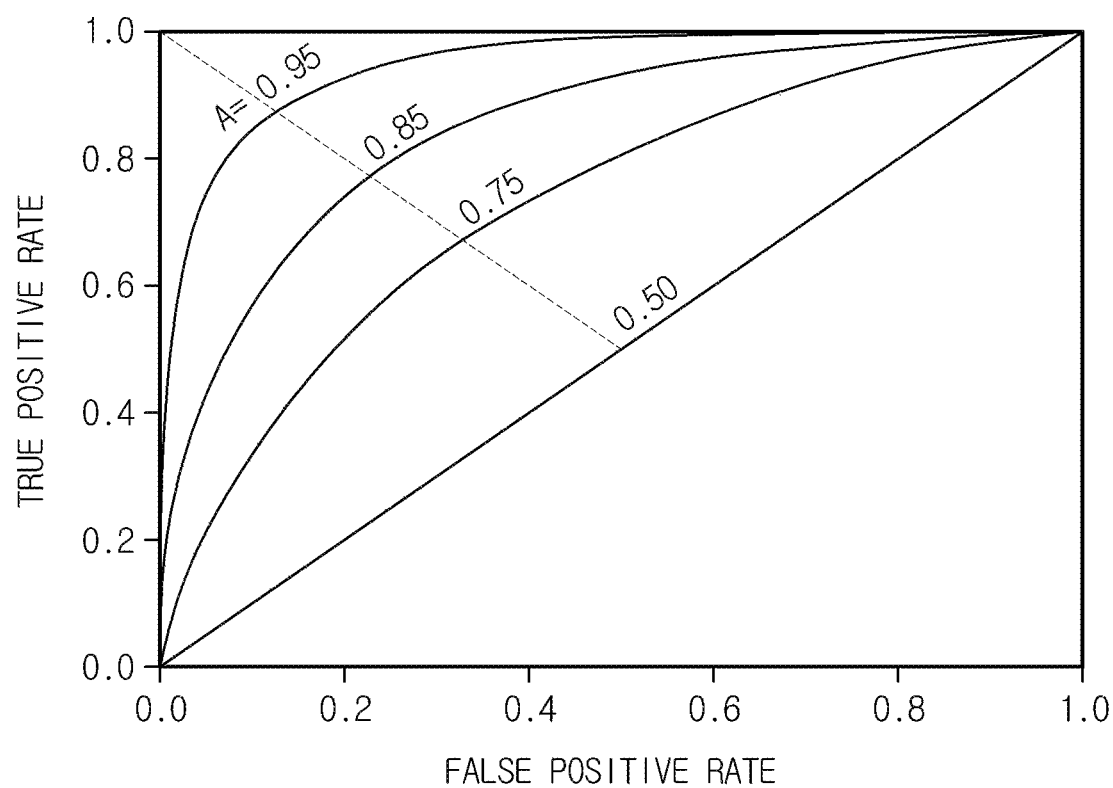
FIG. 1 is a diagram exemplifying ROC curves as a tool for evaluating performance of a logistic regression model that classifies lung cancer patients and normal persons by using complex biomarker group for diagnosing lung cancer selected in accordance with the present invention.

Detailed explanation on the present invention to be made below refer to attached drawings and diagrams illustrated as specific embodiment examples under which the present invention may be implemented to make clear of purposes, technical solutions, and advantages of the present invention. Such example embodiments will be explained fully enough to make those skilled in the art implement the present invention.

In the present specification, "a biospecimen" means a specimen collected from a human body and more desirably it includes body fluids such as blood, blood plasma, serum, lymph, and cerebrospinal fluid and substances secreted, discharged, or collected from the body such as urine, feces, tears, and saliva.

In addition, "an antibody" in the present specification means a specific protein molecule that indicates an antigenic locality and includes all of a polyclonal antibody, a monoclonal antibody, a recombinant antibody, and a fragment capable of binding to an epitope. Particularly, it may be desirable to use the monoclonal antibody among them. Such antibodies may be available if they are produced in use of a prior technology by those skilled in the art. For example, they could also be produced by injecting protein as an immunogen to an external host under a conventional method known to those skilled in the art.

In this specification, "a normal person" is a term intended to indicate a person who is not a lung cancer patient because the term includes a person with a disease except lung cancer.

Additionally, a term "include" and its variations over the detailed explanation and claims of the present invention are not intended to exclude other technical characteristics, additions, components, or steps. Some of other purposes, advantages, and characteristics of the present invention will be disclosed from this specification to those skilled in the art and others will be unveiled from the embodiments of the present invention. The following examples and drawings will be provided as examples and they are not intended to limit the present invention.

Moreover, the present invention covers all possible combinations of example embodiments indicated in this specification. It must be understood that a variety of example embodiments of the present invention are different but they do not need to be mutually exclusive. For example, specific shapes, structures, and characteristics described herein may be implemented with other example embodiments not beyond the spirit and scope of the present invention in relation to one example embodiment. Besides, it must be understood that the positions or placements of individual components in respectively disclosed example embodiments can be changed without being out of the spirit and scope of the present invention. Accordingly, the detailed explanation to be made below will not be taken as a limited meaning and the scope of the present invention, if properly explained, is limited only by the accompanying claims in addition to all scopes equivalent to what the claims argue. Similar reference marks in drawings indicate same or similar functions in several aspects.

Unless indicated in this specification or clearly contextually contradicted, items indicated in a singular form include plural ones.

To make those skilled in the art easily implement the present invention, devices, apparatuses, methods exemplified under the example embodiments of the present invention and results relating thereto are provided.

Types of individual biomarkers used. Individual biomarkers selected in accordance with the present invention may consist of HE4, CEA, ApoA2, RANTES, TTR, and sVCAM-1, but the complex biomarker group selected in accordance with the present invention is not limited to these. For example, some biomarkers may be added to the biomarkers listed above. Whether the individual biomarkers are significant in diagnosing lung cancer must be individually determined but the complex biomarker group including at least HE4, CEA, ApoA2, RANTES, TTR, and sVCAM-1 will be disclosed in this specification. The individual biomarkers selected by the inventors are as follows:

HE4 (Human Epididymis protein 4), as a protein encoded by the WFDC2 gene, is also called as WAP four-disulfide core domain protein 2. The HE4 is conventionally and widely known as a tumor marker for ovarian cancer.

CEA (CarcinoEmbryonic Antigen) is a, glycoprotein involved in cell adhesion. The CEA is normally produced in gastrointestinal tissue during fetal development but the production stops before birth. Accordingly, the CEA is usually present only at a very low level in the blood of healthy adults. However, the level of CEA in a serum may be raised in some types of cancer, which means that it can be used as a tumor marker in clinical tests.

ApoA2 (Apolipoprotein A-II) is a protein encoded by the APOA2 gene in humans. It is the second most abundant protein of the high-density lipoprotein particles.

RANTES {Regulated on Activation, Normal T cell Expressed and Secreted; chemokine (C-C motif) ligand 5} is a protein encoded by the CCL5 gene in humans.

TTR (TransThyRetin) is a transport protein in the serum and cerebrospinal fluid that carries the thyroid hormone thyroxine and retinol-binding protein that binds to retinol. The liver secretes the TTR into the blood and the choroid plexus secretes the TTR into the cerebrospinal fluid.

sVCAM-1 (soluble Vascular Cell Adhesion Molecule-1) is a cell adhesion molecule at a solution state of VCAM-1 that can serve as an important biomarker for inflammatory response when cells are damaged.

In addition to the individual biomarkers as mentioned above, individual biomarkers involved in experiments in the present invention are as follows:

ApoA1 (Apolipoprotein A-I) is a protein that is encoded by the APOA1 gene in humans. This is well-known to have a specific role in lipid metabolism.

B2M (Beta-2 Microglobulin) is a component of MHC class I molecules. In humans, the B2M protein is encoded by the B2M gene.

CA125 (CA-125; Cancer Antigen 125; Carcinoma Antigen 125; or Carbohydrate Antigen 125) is also known as mucin 16 or MUC16 and it is a protein encoded in humans by the MUC16 gene. CA125 has found application as a tumor marker that may be elevated in the blood of some patients with specific types of cancer.

CRP (C-Reactive Protein) is an annular pentameric protein found in blood plasma whose level rises in inflammatory response.

LRG1 (Leucine-Rich alpha-2-Glycoprotein 1) is a protein encoded in humans by the LRG1 gene. The level of the LRG1 is also known to be markedly elevated in acute appendicitis.

Cyfra 21-1 {Cytokeratin 19 Fragment Antigen 21-1; Keratin, type I cytoskeletal 19; cytokeratin-19 (CK-19); or keratin-19 (K19)} is a protein of 40 kDa encoded by the KRT19 gene in humans. The Cyfra 21-1, as a type-I keratin, is known as a biomarker used to detect tumor cells secreted from lymph nodes, peripheral blood, and marrow of breast cancer patients.

Antibodies or kits used to analyze individual biomarkers. To analyze thirteen proteins including HE4, RANTES, sVCAM-1, LRG1, CEA, Cyfra21-1, ApoA2, ApoA1, TTR, B2M, CA125, CA19-9, and CRP, the inventors purchased antibodies or kits from several manufacturers. The information on suppliers including antibodies, kits, standard substances (standard proteins), etc. is shown in tables 1 and 2 below.

TABLE 1

| Biomarker | Standard Substance Maker | Antibody Maker 1 | Antibody Maker 2 |
|---|---|---|---|
| HE4 | XEMA | XEMA | XEMA |
| RANTES | PeproTech | R&D Systems | R&D Systems |
| sVCAM-1 | R&D Systems | R&D Systems | R&D Systems |
| LRG1 | R&D Systems | R&D Systems | R&D Systems |

TABLE 2

| Biomarker | Main Reagent | Calibrator | Maker |
|---|---|---|---|
| CEA | Elecsys CEA | CEA CalSet | Roche |
| Cyfra21-1 | Elecsys CYFRA 21-1 | CYFRA 21-1 CalSet | Roche |
| ApoA2 | Apo A-2 Auto ·N "Daiichi" | Apo auto N Daiichi | Sekisui |
| ApoA1 | Apo A-1 Auto ·N "Daiichi" | Apo auto N Daiichi | Siemens |
| TTR | N Antiserum to human PreAlbumin | N Protein standard SL | Siemens |
| B2M | Tina-quant β2-microglobulin | β2-Microglobulin Calibrator | Roche |
| CA125 | Elecsys CA 125 II | CA 125 II CalSet | Roche |
| CA19-9 | Elecsys CA 19-9 | CA 19-9 CalSet | Roche |
| CRP | CardioPhase hsCRP | N Rheumatology standard SL | Siemens |

In case of standard protein products, HE4 and RANTES were purchased, respectively, from XEMA and PeproTech while sVCAM-1 and LRG-1 were purchased from R&D Systems. In case of reagents and calibrators, CEA, Cyfra21-1, B2M, CA125 and CA19-9 were purchased from Roche while ApoA1 and ApoA2 were bought from Sekisui and TTR and CRP from Siemens.

Collection of blood serum specimens of lung cancer patients. Peripheral blood specimens were collected from a total of 355 lung cancer patients (242 patients from Asan Medical Center and 113 from Keimyung University Dongsan Medical Center) including 162 patients with stage I lung cancer, 42 with stage II lung cancer, 62 with stage III lung cancer, and 89 with stage IV lung cancer. When patients were divided depending on their medical history, they included 230 patients with adenocarcinoma, 109 with squamous cell carcinoma, 4 with large cell carcinoma, 2 with neuroendocrine carcinoma, and 10 with others. According to gender, 139 patients were male and 216 were female and the average age of the patients was 63.85 years with the median age of 66 years. The range was 25 to 83 years.

The lung cancer patients herein were confirmed to have lung cancer by using the well-known methods, which include chest PA X-ray, chest CT, ultrasonography, MRI, PET, pulmonary function test, lung perfusion scan, lung biopsy {CT guided percutaneous needle aspiration (PCNA)}, pleural effusion and pleural biopsy, including biomolecular examination which has testing of EGFR mutation, gene copy number, level of expression, K-ras mutation, and EML4-ALK fusion oncogene but those skilled in the art would know well that tests are not limited to these.

Collection of blood serum specimens of a control group. Peripheral blood specimens were collected from a total of 590 normal subjects from the Department of Family Medicine, Seoul National University Hospital. According to gender, 274 people were male and 343 were female and the average age of the patients was 56.87 years with the median age of 56 years. The range was between 38 and 79 years.

Both lung cancer patients and the control group had their blood taken by using a well-known tool called Vacutainer SST II tube (Becton Dickinson) and their blood was centrifuged to separate serum.

Measuring and building result database. The protein expression levels of the individual biomarkers were measured with the collected serum specimens and accordingly a database with the measured data were built. The determination methods used for these are as follows:

Protein Determination with Regard to HE4 and LRG-1

First of all, HE4 and LRG-1 were measured under the Enzyme-Linked ImmunoSorbent Assay (ELISA). As well known to those skilled in the art, the ELISA is a test under which antibodies label antigens with enzymes and it estimates the activation of enzymes to measure strength and amount of antigen-antibody reactions. The biotinylated detection antibodies were labeled and used. The specific steps for implementing the ELISA protocol were as follows:

Labeling detection antibodies with biotin. To biotinylate detection antibodies used under the ELISA protocol for quantifying HE4 and LRG-1, a reagent EZ-Link Sulfo-NHS-LC-Biotin (sulfosuccinimidyl-6-[biotin-amido] hexanoate; ThermoFisher Scientific, Waltham, Mass.) was used and the test was conducted under the method recommended by the maker. Briefly, 400 μg of the anti-human HE4 antibody (XEMA Co. Ltd., Moscow, Russia) or the anti-human LRG-1 antibody (R&D systems, Minneapolis, Minn.) was prepared in 400 μl of the PBS solution and a 10 mM Sulfo-NHS-LC-Biotin solution was put in it at the antibody-mole ratio of 1:20 before it was reacted for 30 minutes at room temperature. When the antibodies were completely labeled with the biotin, each one liter of the PBS solution was dialyzed three times and then kept at −80° C. until it was dispensed and used.

ELISA Protocol for HE4 and LRG-1. HE4 and LRG-1 were quantified under the ELISA protocol. In brief, after being put in the 96-well microplate (Nalgene Nunc Inc., Rochester N.Y.), 100 μl of the capture antibody specific for human HE4 (capture antibody; XEMA Co. Ltd., Moscow, Russia) at the concentration of 1 μg/ml was applied at 4° C. overnight. After being cleaned three times with the cleaning solution (PBS with 0.05% Tween 20), the PBS solution with 5% skim milk was put in the wells and stirred for 2 hours at room temperature to block non-specific binding. After being cleaned three times with the cleaning solution, 100 μl of blood serum or a standard calibrator was added in each well and it was reacted for one hour at room temperature before being cleansed three times. A biotinylated detection antibody prepared above was treated at the concentration of 1 μg/ml and reacted for one hour again at room temperature. After being cleaned three times, 0.5 μg/ml of streptavidin-horseradish-peroxidase (Sigma-Aldrich, St. Louis, Mo.) was added and then reacted for 30 minutes at room temperature before being cleaned five times again. To induce color reaction, 100 μl of tetramethylbenzidine (TMB; KPL, Gaithersburg, Md.) was added each. After 15 minutes, the reaction was stopped with 50 μl of the 2N sulphuric acid. Absorbance was measured at 450 nm by using a microplate reader (Emax; Molecular Devices LLC., Sunnyvale, Calif.). The result was analyzed by using a 5-parametric curve fitting with a molecular device SoftMax Pro Software. The HE4 standard protein for calibration and the LRG-1 standard protein were purchased, respectively, from XEMA and R&D.

Protein Determination with Regard to RANTES and sVCAM-1

Next, the concentration levels of RANTES and sVCAM-1 in blood serums of lung cancer patients and normal people were measured under a multiplex immunoassay method using the xMAP technology platform (Luminex Corp. Austin, Tex.). The multiplex immunoassay method, which saves time and costs compared to conventional analysis methods such as ELISA, western blotting, and polymerase chain reaction (PCR), is an analytic method known to those skilled in the art. Herein, capture antibodies were used by being coupled to MagPlex microspheres in a carbodiimide method and the microspheres' exposure to light was minimized during the whole course.

Coupling between antibodies and microspheres. The process of protein determining on RANTES and sVCAM-1 was conducted under the protocols recommended by manufacturers. First of all, MagPlex microsphere suspension (by Luminex Corp.), after being vortexed, was suspended for 20 seconds in a sonification bath (made by Sonicor Instrument Corporation, USA). After being moved to a microtube, 1×106 microspheres were separated using magnets. After the solution was removed, they were cleaned with 100 μl of distilled water and then again re-suspended to 80 μl of a 0.1 M sodium phosphate buffer (pH 6.2). After that, 50 mg/ml of N-hydroxy-sulfosuccinimide (Sulfo-NHS; ThermoFisher Scientific, Waltham, Mass.) and 1-ethyl-3-(3-dimethylaminopropyl)-carbodiimide hydrochloride (ThermoFisher Scientific) were added by 10 μl each at a time and mixed at an interval of 10 minutes for 20 minutes at room temperature. After being cleaned twice with 250 μl of 50 mM MES, pH 5.0, the microspheres were re-suspended with 100 μl of the 50 mM MES. To the microspheres activated by carboxyl groups, 10 μg of antibodies (anti-sVCAM-1 or anti-RANTES) is added and then the 50 mM MES to get to 500 μl. After that, the mixture was mixed for 2 hours at room temperature. The microspheres through the antibody coupling reaction were cleaned twice with 500 μl of PBS-TBN (PBS, 1% BSA, 0.02% Tween 20, 0.05% sodium azide) and counted with a hemocytometer. The antibodies-coupled microspheres were kept in a dark room at temperature between 2 and 8° C. at concentration of 1×106/500 μl of PBS-TBN.

sVCAM-1 and RANTES multiplex immunoassays. The serum concentration levels of sVCAM and RANTES were quantified at the same time by using the antibody-coupled microspheres under multiplex assays. More specifically, after being mixed, 20 μl of RANTES standard protein (R&D Systems) and sVCAM-1 standard protein (PeproTech, Rocky Hill, N.J.) or blood serum and 20 μl of the mixed solution of capture antibody-coupled microspheres in individual wells of the 96-well microplate specific for two protein biomarkers RANTES and sVCAM-1 were reacted for one hour at room temperature. Since then, 20 μl of the biotinylated detection antibody was added and then reacted for one hour and 20 μl of Streptavidin R-Phycoerythrin (Jackson ImmunoResearch) was added and then reacted for 30 minutes, in serial order. Thereafter, the plate was washed twice with PBST (0.05% Tween 20, PBS) solution using a microplate washer (HydroFlex™; TECAN, Switzerland) and then the microspheres were re-suspended with 100 μl of the same buffer solution to measure strength of fluorescence using Luminex™200. The blood serum concentration levels of sVCAM-1 and RANTES proteins were analyzed by using a 5-parametric curve fitting with Beadview Software by Upstate (USA).

Protein Determination with Regard to CEA, Cyfra 21-1, CA125, CA19-9, ApoA1, ApoA2, B2M, TTR, and CRP CEA, Cyfra21-1, CA125 and CA19-9 under an electrochemiluminescence immunoassay with Cobas e601 (Hoffmann-La Roche A G., Switzerland); ApoA1, ApoA2 and B2M under a turbidimetric immunoassay with Clinical Analyzer 7080 (Hitachi Medical Corp., Japan); and TTR and CRP under a turbidimetric immunoassay with BN2 System (Siemens A G., Germany) were measured under manufacturers' manuals.

Statistical Proofs with Regard to Efficacy of Biomarkers

Experimental values of the determined protein acquired through the aforementioned measurement may be used for statistical analysis after being preprocessed, to be explained below. Herein, preprocessing may refer to a log (base 10) transformation of the experimental values. In this example embodiment, since the experimental values tend to cluster toward the right side, the log transformation was used for the experimental values of all individual biomarkers to relieve such a tendency. Unless otherwise stated in one example embodiment explained in this specification, such log-transformed data would be used.

The log-transformed data were analyzed by using bioinformatics and an R Statistical Package {R Development Core Team (2007). R: A language and environment for statistical computing. R Foundation for Statistical Computing, Vienna, Austria. ISBN 3-900051-07-0, URL http://www.R-project.org.}. Through the following analysis, a model of diagnosing lung cancer was created from the inputted data.

One example of a model of diagnosing lung cancer— analysis of binary logistic regression. While common linear regression analysis is used when dependent variables are continuous, logistic regression analysis is used when dependent variables are dichotomous or binary such as success/failure, good/poor, or cancer/no cancer. The logistic regression analysis model is as shown below.

$$\ln\left(\frac{p_j}{1-p_i}\right) = \alpha + \beta_1 x_{1i} + \beta_2 x_{2i} + \ldots + \beta_p x_{pi} + e_i,$$

$$e_i \sim \text{Normal}(0, \sigma^2)$$

where Pi=P(yi=1) has a value between 0 and 1; and yi has a value which is either 0 or 1. In this specification, 0 was set as no lung cancer and 1 as lung cancer. In addition, $x_k$ refers to experimental values (logarithmic values) of individual biomarkers selected to detect lung cancer. The R Statistical Package, for example, can perform logistic regression by commands as shown below and consequently, a model object is derived as a regression model.

$$m<-glm(b\sim x1+x2+x3+x4+x5+x6, \text{family=binomial})$$

Because whether individual subjects have lung cancer or not can be determined with the model object m, this regression model can be regarded as a model of diagnosing lung cancer. Herein, b is a dichotomous factor (TRUE=lung cancer, FALSE=normal) and x1, x2, x3, x4, x5, and x6 are predictor variables. For example, x1, x2, x3, x4, x5, and x6 may be expression levels of CEA, HE4, ApoA2, TTR, sVCAM-1, and RANTES, respectively. In this case, it would be possible to predict whether individual subjects are lung cancer patients or not from the measurement data from the individual subjects. For example, commands of the R Statistical Package which perform the prediction may be as shown below.

$$dfrm<-\text{data.frame}(x1=\text{value}, x2=\text{value}, x3=\text{value},$$
$$x4=\text{value}, x5=\text{value}, x6=\text{value})$$

$$\text{predict}(m, \text{type="response"}, \text{newdata}=dfrm)$$

The inventors acquired a logistic regression model by executing logistic regression mentioned above for a variety of complex biomarker groups to be explained below. More specifically, to verify the validity of the logistic regression model, the inventors used 10-fold cross validation. In the 10-fold cross validation, data are divided randomly into 10 segments. With one segment reserved as test data, the other nine segments are used for training thereby creating the logistic regression model and then the prediction, i.e., a verification, as stated above is implemented by using the one segment. The aforementioned courses are executed repeatedly for all the segments. The performance of the prediction may be confirmed by integrating the result of the prediction. An ROC curve is one of tools for this.

A performance of a model of diagnosing lung cancer— ROC curves. As the aforementioned lung cancer detection model serves as a kind of classifier, the performance can be confirmed through receiver operating characteristic curves, i.e., ROC curves, that show the performance of the classifier.

FIG. 1 is a diagram exemplifying ROC curves as a tool for evaluating performance of a logistic regression model. By referring to FIG. 1, first of all, the horizontal axis represents "1−specificity=false positive rate" where the specificity is a value defined as follows: specificity=true negative/(false positive+true negative). In other words, the specificity means a probability of determining 'negative thing' as negative. Thus, as the curve in the graph becomes inclined toward the left, a rate of misjudgment, i.e., a rate of determining 'positive thing' as negative, is reduced. In addition, the vertical axis represents "sensitivity", i.e., a true positive rate, where the sensitivity is defined as true positive/(true positive+false negative). In other words, since the sensitivity means a rate of determining 'positive thing' as positive, as the curve in the graph becomes inclined upwards, a rate of misjudgment, i.e., a rate of determining 'negative thing' as positive, is reduced. Accordingly, as the performance of a classifier becomes better, the area under the curve (AUC) increases. If the classifier does not have any capability of classification, the AUC becomes 0.5. In general, the performance of the classifier can be determined by referring to the following AUC values: non-informative (AUC=0.5), less accurate (0.5<AUC≤0.7), moderately accurate (0.7<AUC≤0.9), highly accurate (0.9<AUC<1), and perfect (AUC=1).

Performance validation of the model of diagnosing lung cancer (ROC-AUC). Under the null hypothesis of AUC=0.5 that there is no classification performance of the model of diagnosing lung cancer in the invention and the alternative hypothesis that the logistic regression model has classification performance, hypothesis verification can be performed. If a p-value, i.e., a probability of error, is lower than a certain probability, then the null hypothesis is rejected and the alternative hypothesis is adopted. The certain probability is called a significance level. In statistics, 0.05 is generally chosen as the significance level. The performance of the model of diagnosing lung cancer can be verified by using the method of considering AUC of the ROC. Next, a process of creating the model of diagnosing lung cancer will be explained.

Figure 2:
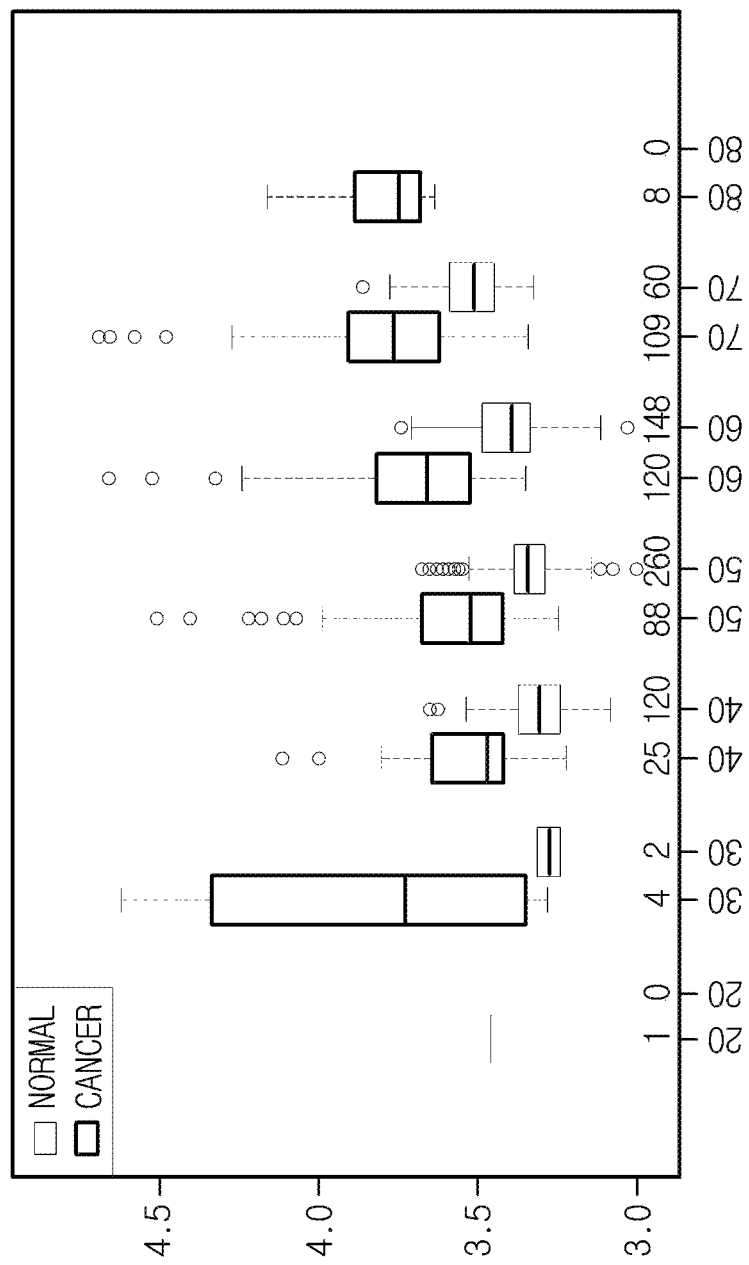
FIG. 2 is a graph illustrating correlations between subjects' ages and expression levels of HE4 (which is one of individual biomarkers in the complex biomarker group selected in accordance with the present invention) in specimens of lung cancer patients and normal persons.

Correlations between HE4 and ages of subjects were considered. (Unless otherwise stated, all values of HE4 are calibrated.) FIG. 2 is a graph illustrating correlations between expression level of HE4 and ages of subjects. By referring to FIG. 2, it can be found that there are positive correlations between HE4 expression level and ages of subjects. In the figure, the value of Pearson correlation coefficient is 0.490 and the p-value is less than 2.2e-16. In the diagram, the correlations between ages and the expression level of HE4 are shown. To evaluate the effectiveness of HE4, "calibrated" expression level whose value is acquired by removing influences of ages from the expression level of HE4 can be drawn. In case of HE4, estimated values of $\beta_0$ and $\beta_1$ included in a following formula: $(HEA)=\beta_0+\beta_1 \times (age)+\epsilon$ are drawn through regression analysis. If the estimated values are defined respectively as $\hat{\beta}_0$ and $\hat{\beta}_1$, a residual value for HE4 can be defined as follows: (residual of HEA)=$(HEA)-\hat{\beta}_0-\hat{\beta}_1 \times (age)$.

Course of Election of Individual Biomarkers in Accordance with the Present Invention First of all, the inventors selected 120 candidate protein markers among more than tens of thousands of proteins existing in human bodies, and picked out over 50 out of 120 markers considering clinical significance, easiness of analysis, accuracy of algorithm, costs, clinical circumstances, and other situations through reviewing of domestic and international academic articles and literature, 2D electrophoresis (2D Gel), SELDI-TOF MS, etc. We chose thirteen final candidate markers which are expected to be appropriate to be included in the present invention by verifying effectiveness through statistical analyses of approximately 600 lung cancer patients and roughly 900 normal subjects twice. More specifically, through a course just as described in an article such as Breast Cancer Research 2009, 11, R22 or an article in Journal of Thoracic, Cardiac & Vascular Surgery 2012:143;421-7, it could be introduced that 50 out of 120 protein markers are selected and then again thirteen markers are chosen therefrom, but it would not be limited to this.

The inventors successfully found the most excellent subset that are desirable to be included in a statistical model of the present invention among the thirteen individual biomarkers selected as the final candidates and two demographical variables by using aforementioned experimental data (for training). In this study conducted by the inventors, "six biomarkers" out of thirteen individual biomarkers and "age" out of the two demographical variables were carefully selected. Specifically, the complex biomarker group was selected in accordance with the present invention by using 515 specimens of normal persons and 280 specimens of cancer patients as training data: 113 specimens of NSCLC patients from Keimyung University Dongsan Medical Center, 167 specimens of NSCLC patients from Asan Medical Center, and the 515 specimens from Department of Family Medicine, Seoul National University Hospital. To validate the complex biomarker group selected in accordance with the present invention, test data were used. The test data consisted of 75 specimens of NSCLC patients from Asan Medical Center and 75 specimens of normal persons from Department of Family Medicine, Seoul National University Hospital. HE4, CEA, ApoA2, TTR, sVCAM-1, and RANTES were included while ApoA1, B2M, CA125, CA19-9, CRP, Cyfra21-1, and LRG1 were removed. These will be explained later.

For the convenience of explanation, the six biomarkers selected in accordance with the present invention are designated as "BI combination" and the twelve biomarkers out of the thirteen individual biomarkers except CA19-9 and age out of the two demographical variables except gender are designated as "Full combination."

The reasons for selecting the "BI combination" are as follows:

First of all, a chi-square test and a Student's t-test were used to evaluate significance of the thirteen individual biomarkers and the two demographical variables.

Removal of a biomarker CA19-9 and gender. At this stage, the biomarker CA19-9 and the gender were removed. Under the significance level of 0.05, a relationship between the gender and whether subjects are lung cancer patients or not was not significant (p-value: 0.314). In addition, a difference between a mean of a control group and that of an experimental group with regard to CA19-9 was not significant (p-value: 0.2829). For reference, Table 3 below shows results of chi-square test under a null hypothesis that the gender and whether subjects are lung cancer patients are independent, and Table 4 shows results of Student's t-test under a null hypothesis that a true value of a difference between a mean of the control group and that of the experimental group is 0.

TABLE 3

|  | X-squared | df | p-value |
| --- | --- | --- | --- |
| sex | 1.013 | 1 | 0.314 |

TABLE 4

|  | t | df | p-value |
| --- | --- | --- | --- |
| HE4 | −14.506 | 346.247 | <2.2e−16 |
| Cyfra21-1 | −10.595 | 397.976 | <2.2e−16 |
| CEA | −11.531 | 374.846 | <2.2e−16 |
| ApoA2 | 18.050 | 358.791 | <2.2e−16 |
| RANTES | 17.981 | 404.302 | <2.2e−16 |
| TTR | 16.04, | 373.111 | <2.2e−16 |
| ApoA1 | 11.649 | 425.734 | <2.2e−16 |
| LRG1 | −11.418 | 377.333 | <2.2e−16 |
| CRP | −11.381 | 461.46 | <2.2e−16 |
| B2M | −10.160 | 388.398 | <2.2e−16 |
| CA125 | −7.983 | 353.087 | 2.022e−14 |
| sVCAM-1 | 2.348 | 494.999 | 0.01928 |
| CA19-9 | −1.075 | 401.249 | 0.2829 |
| age | −10.206 | 513.367 | <2.2e−16 |

If effects due to individual biomarkers except a biomarker A are removed from effects due to all the biomarkers in the Full combination, i.e., if a residual value of the biomarker A expected by linear combination of experimental data of the individual biomarkers except the biomarker A is considered, then it can be checked whether the biomarker A has a significant effect of distinguishing the experimental group and the control group.

Explaining more specifically, if individual biomarkers belonging to the Full combination are indicated as biomarkers $B_i$, a value of the biomarker A can be drawn by linear regression analysis as follows:

$$(\text{a value of biomarker } A) = \widehat{\beta_0} + \Sigma_{1 \leq i \leq 12, B_i \neq A}(\widehat{\beta_i} \times B_i) + \hat{\beta}_{age} \times (\text{age}) + \hat{\epsilon}$$

Herein, the residual value $(\hat{\epsilon})$ of the biomarker A acquired by subtracting parts due to the biomarkers $B_i$ except the biomarker A and the age from the value of the biomarker A is as follows:

$$(\text{the residual value } (\hat{\epsilon}) \text{ of biomarker } A) = (\text{the value of biomarker } A) - \{\widehat{\beta_0} + \Sigma_{1 \leq i \leq 12, B_i \neq A}(\widehat{\beta_i} \times B_i) + \hat{\beta}_{age} \times (\text{age})\}.$$

In a similar way, the residual value $(\hat{\epsilon})$ of the age acquired by subtracting elements due to the biomarkers $B_i$ from the value of the age is as follows:

$$(\text{the residual value } (\hat{\epsilon}) \text{ of age}) = (\text{the value of age}) - \{\widehat{\beta_0} + \Sigma_{1 \leq i \leq 12}(\widehat{\beta_i} \times B_i)\}.$$

To verify significance of individual biomarkers, the inventors conducted Student's t-test with regard to the residual values. Herein, the Student's t-test had the null hypothesis that there is no difference between a mean residual value of the control group ("the mean value of the control group") and a mean residual value of the experimental group ("the mean value of the experimental group") and the result is shown in Table 5 below.

TABLE 5

|  | t | Df | p-value |
|---|---|---|---|
| Residual of ApoA2 | 2.212 | 339.715 | 0.02763 |
| Residual of CEA | −2.3571 | 382.544 | 0.01892 |
| Residual of TTR | 3.8573 | 433.241 | 0.000132 |
| Residual of age | −2.4912 | 476.473 | 0.01307 |
| Residual of Scam.1 | 5.5713 | 569.164 | 3.905e−08 |
| Residual of RANTES | 7.2481 | 404.082 | 2.164e−12 |
| Residual of HE4 | −3.4939 | 377.336 | 0.0005324 |
| Residual of ApoA1 | 1.1119 | 415.886 | 0.2668 |
| Residual of B2M | −1.1363 | 450.711 | 0.2564 |
| Residual of CA125 | −0.029 | 396.394 | 0.9769 |
| Residual of CRP | −1.6235 | 553.462 | 0.105 |
| Residual of CYFRA21-1 | −0.7355 | 421.892 | 0.4624 |
| Residual of LRG1 | 1.5905 | 479.893 | 0.1124 |

By referring to Table 5, as for HE4, CEA, ApoA2, TTR, sVCAM-1, and RANTES belonging to the BI combination, since the p-values thereof were less than the significance level of 0.05, there was a difference between the mean residual value of the control group and that of the experimental group. Thus, the significance of the above-mentioned biomarkers could be confirmed. Compared to this, however, ApoA1, B2M, CA125, CA19-9, CRP, Cyfra21-1, and LRG1 which are not belonging to the BI combination in the Full combination were not significant because the p-values thereof were more than the significance level of 0.05. In other words, the rest of biomarkers which are not selected as the BI combination were not significant, i.e., not good, as classifiers for the lung cancer patients and the control group.

Figure 3:
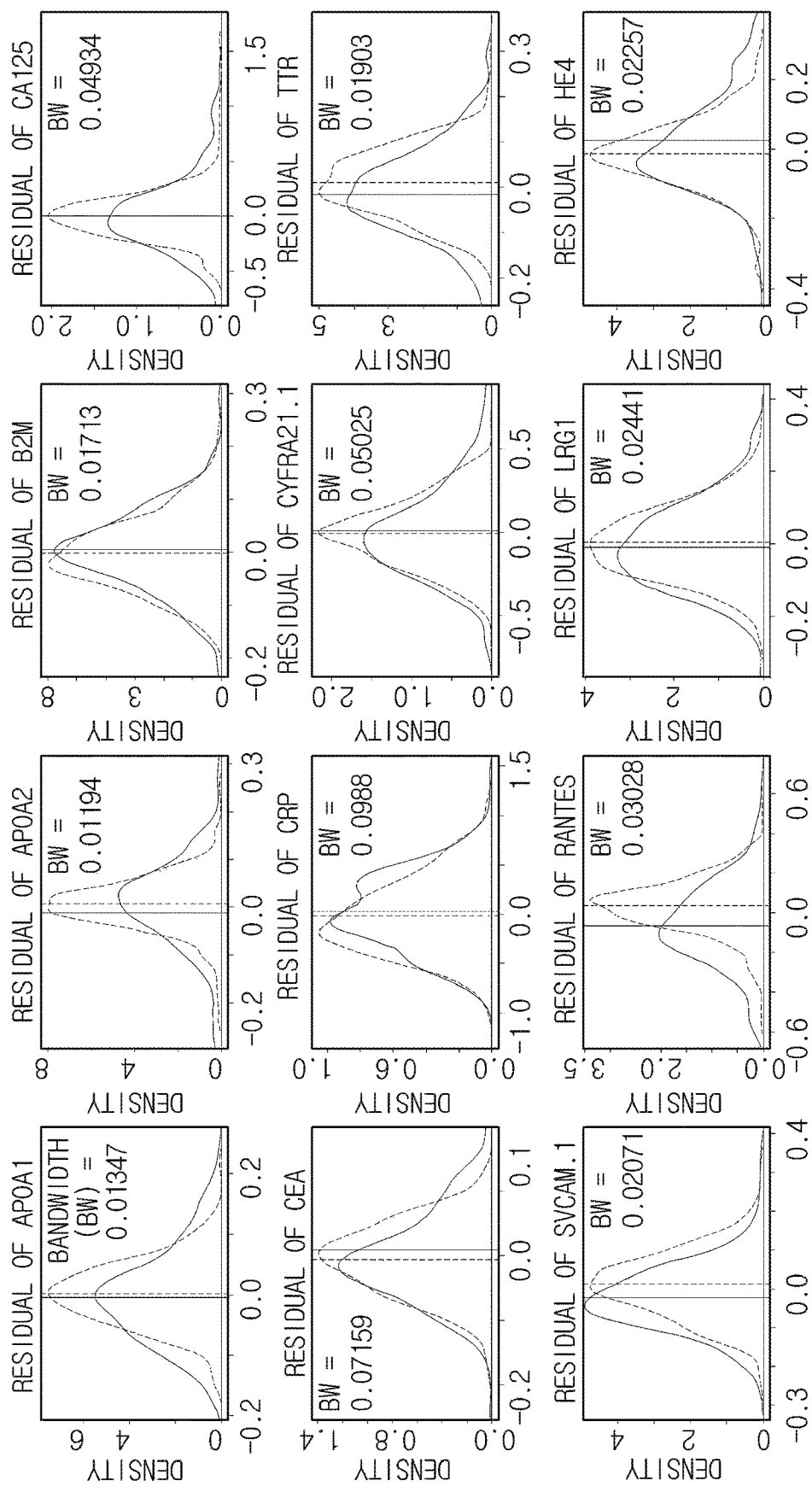
FIG. 3 shows one example embodiment of density plots that represent data measured for specimens of lung cancer patients and normal persons by using individual biomarkers in the present invention, wherein the density plots are acquired by the individual biomarkers after removing the influences of the other biomarkers and the ages.
Figure 4:
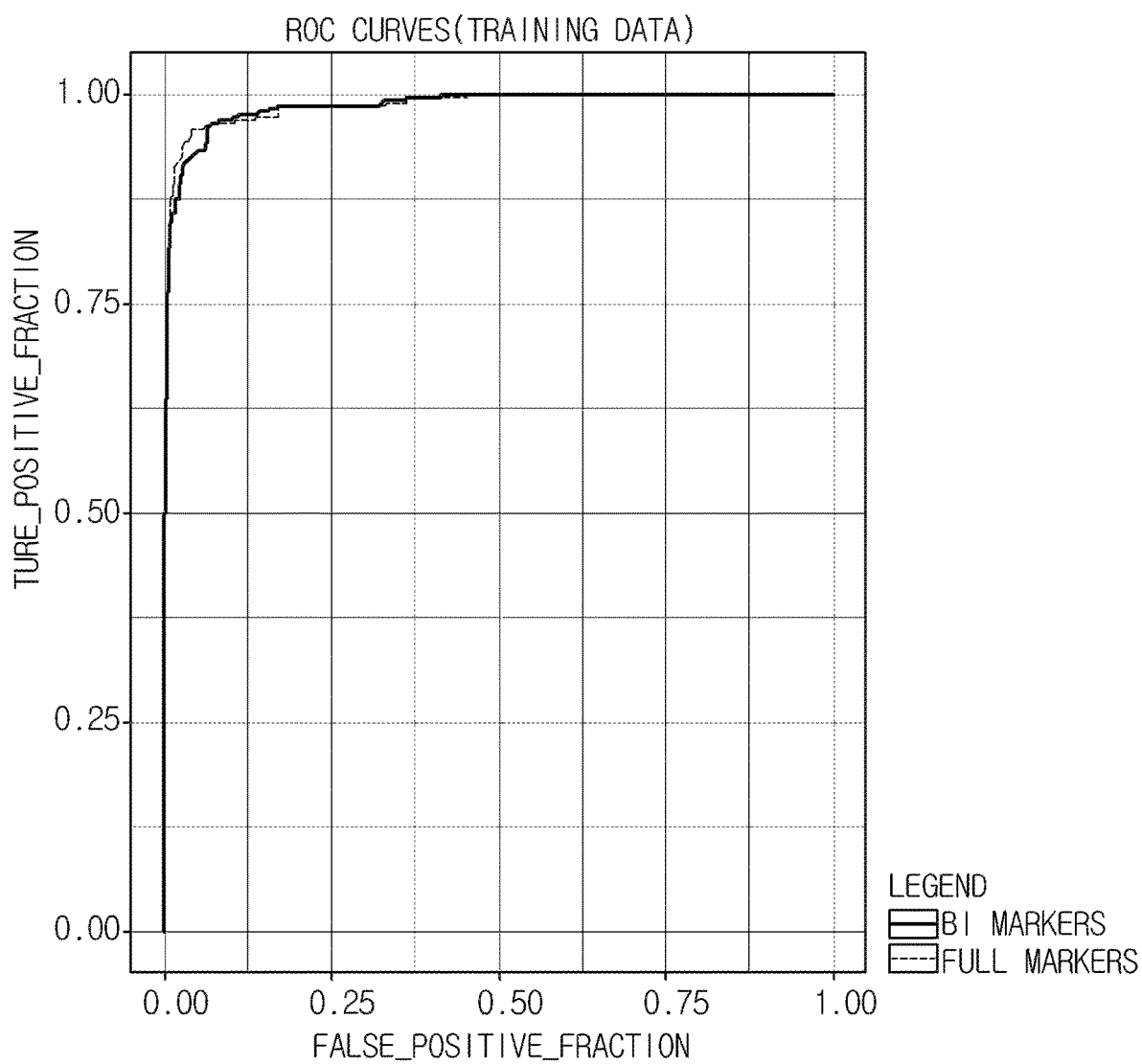
FIG. 4 is a drawing exemplarily illustrating ROC curves for training data sets as indicators for evaluating (i) complex biomarker group selected in accordance with the present invention and (ii) a combination of all biomarkers including twelve individual biomarkers used for experiments in accordance with the present invention.

The results in Table 5 can be visually confirmed in FIG. 3. FIG. 3 shows density plots that indicate the residual values of the individual biomarkers. Of the respective two density plots, solid lines are graphs for the lung cancer patients while dotted lines are for the control group (normal persons). The mean values of the lung cancer patients are indicated in solid vertical lines and those of the control group are indicated in dotted vertical lines. It can be found that respective difference values between the respective mean values of the lung cancer patients and those of the control group are relatively significant for the individual biomarkers belonging to the BI combination in accordance with the present invention. Further, in FIG. 3, it can be found visually that the individual biomarkers belonging to the BI combination in accordance with the present invention are relatively better markers for diagnosing lung cancer than those not belonging to the BI combination. In other words, the experiments and analyses conducted by the inventors proved that it is more favorable to use the BI combination than to use the Full combination. ROC curves of the training data set are illustrated in FIG. 4 and AUC (0.9868239) of the ROC curve when the Full combination is used is similar to AUC (0.9864008) when the BI combination is used, as mentioned in FIG. 6. That is, even though the BI combination had only six individual biomarkers after the other six ones were excluded from the 12 in Full combination, the AUC of the BI combination was almost identical to that of the Full combination. Thus, it was found that the same effect could be obtained more economically.

TABLE 6

|  | AUC | p-value |
|---|---|---|
| Full combination | 0.9868239 | 2.350115e−114 |
| BI combination | 0.9864008 | 3.679639e−114 |

Figure 5:
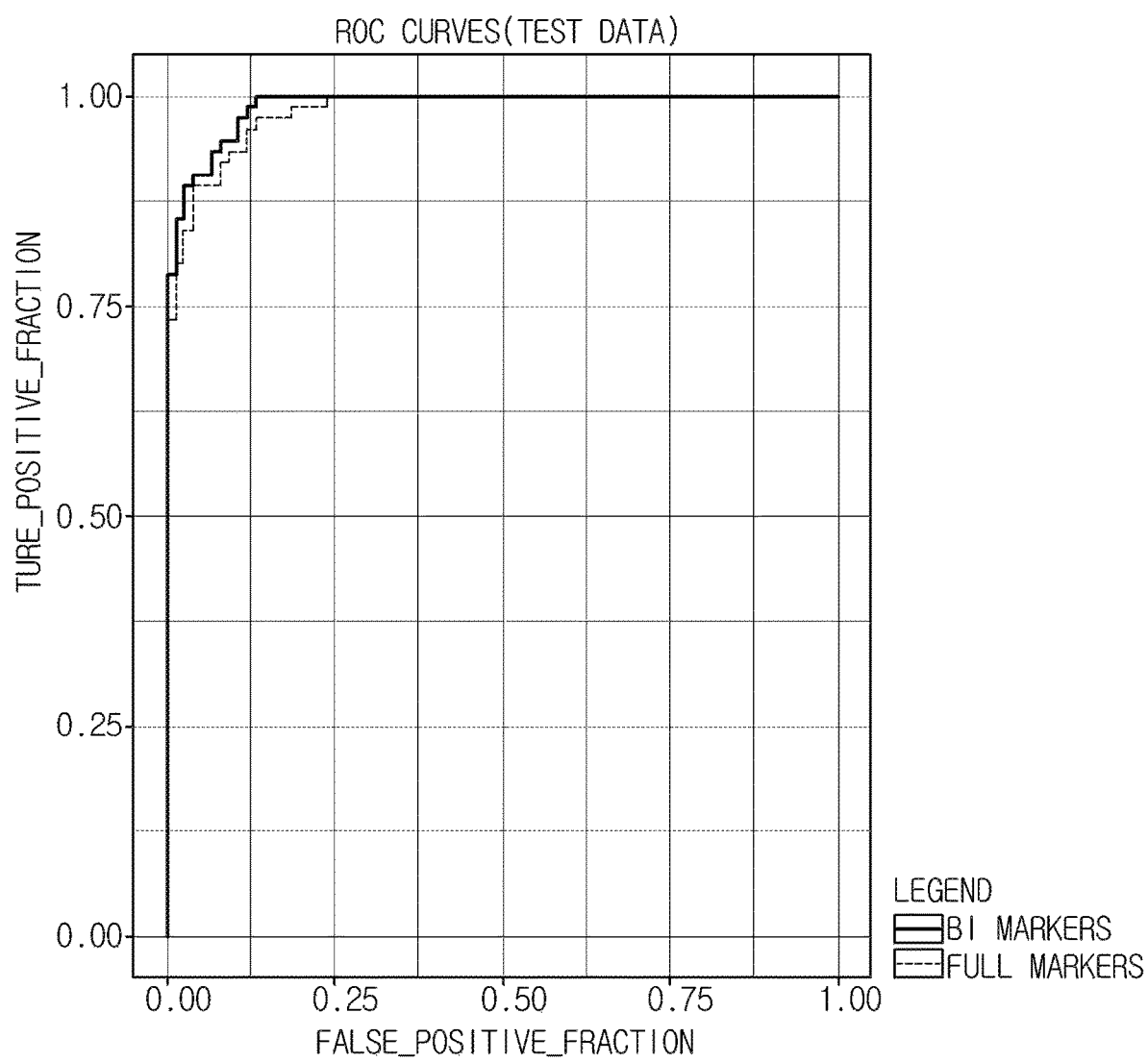
FIG. 5 is a drawing exemplarily illustrating ROC curves for test data sets as indicators for evaluating (i) the complex biomarker group selected in accordance with the present invention and (ii) the combination of all biomarkers including the twelve individual biomarkers used for experiments in accordance with the present invention.
Figure 7:
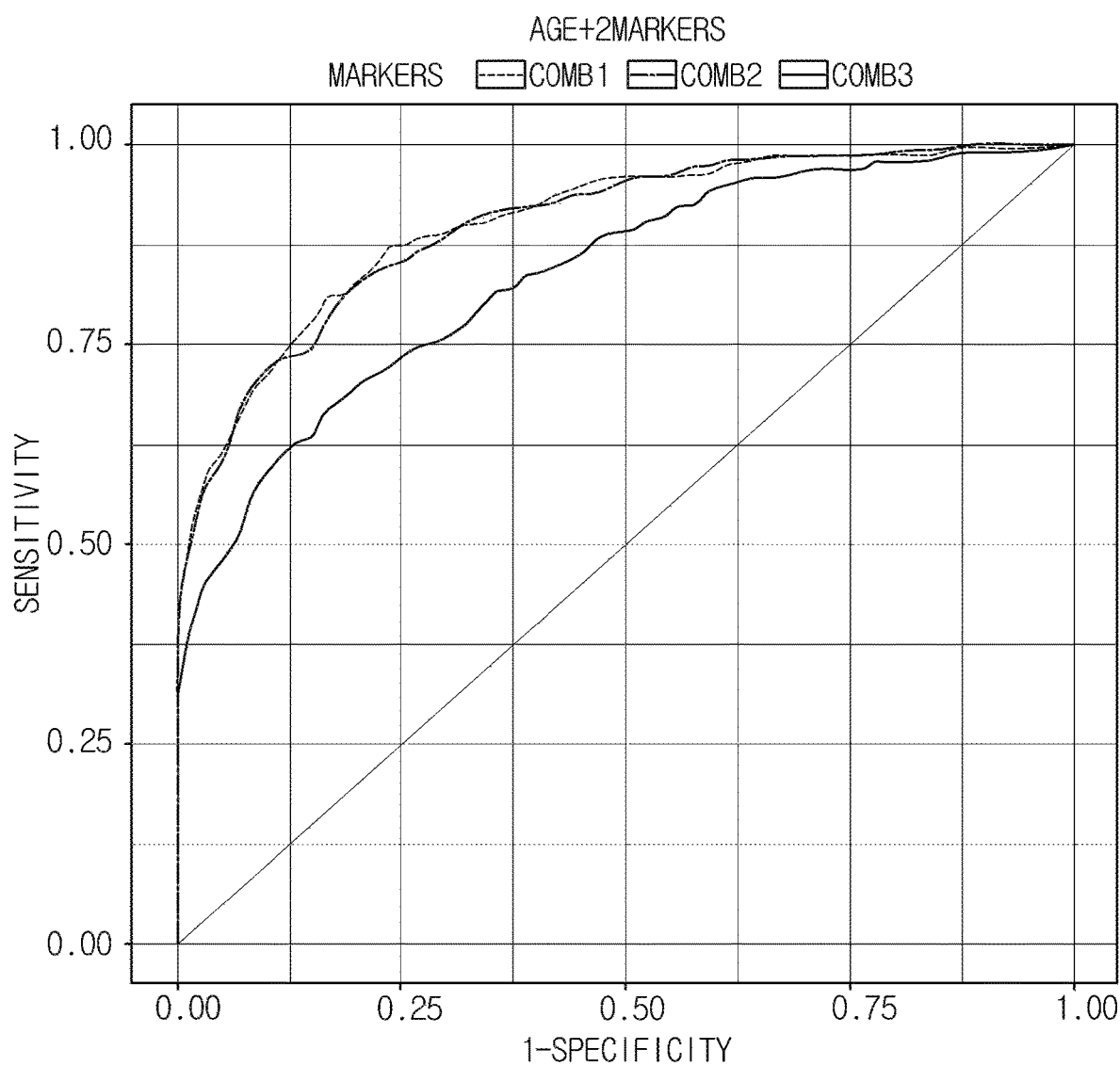

Besides, given the prediction with test data set, as indicated in FIG. 7, it was found that the performance of the BI combination (AUC=0.9884444) is better than that of the Full combination (AUC=0.9818667). Thus, it can be found that the BI combination are more favorable than the Full combination. The ROC curves for the test data set are illustrated in FIG. 5.

TABLE 7

|  | AUC | p-value |
|---|---|---|
| Full combination | 0.9818667 | 1.143172e−24 |
| BI combination | 0.9884444 | 2.709566e−25 |

The performance of the classifiers with the BI combination was assessed using 10-fold cross validation on the training data set and the test data set.

As such, the performance of the classifiers by using exemplary complex biomarker group under the methodology proposed by the inventors appears roughly in Table 8 as shown below. The exemplary complex biomarker group-considered HE4, CEA, ApoA2, RANTES, TTR, sVCAM-1 and ages of subjects.

TABLE 8

| Algorithm | AUC | Condition | sensitivity | Stage 1 | 2 | 3 | 4 |
|---|---|---|---|---|---|---|---|
| GLM | 0.988 (p-value: 0.000) | specificity 93.90% (cutoff = 0.3700928) | 94.65% | 91.98% | 97.62% | 93.55% | 98.88% |

In Table 8, the algorithm used in the classifier is a Generalized Linear Model (GLM), particularly, the logistic regression model. The AUC was 0.988 with the p-value of 0.000 and the sensitivity level of 94.65%. Even for patients with stage I lung cancer, it can be found that the lung cancer was diagnosed with a high sensitivity level of 91.98%. Herein, the specificity level was 93.90%, at which time, the threshold or cutoff was 0.3700928. The cutoff point was so selected that the sensitivity levels were at least 90% and the specificity levels were high enough in all stages of lung cancer progression. Explaining the reason for the selection more specifically, the best accuracy can be influenced by the number of samples, but in the experiment in this specification, as the number of samples of the normal persons was relatively higher than the number of samples of the lung cancer patients, the point with the high specificity was the point with the best accuracy. In conclusion, it shows a statistically significant performance by declining the null hypothesis (AUC=0.5) with the p-value of 0.000.

Figure 9:
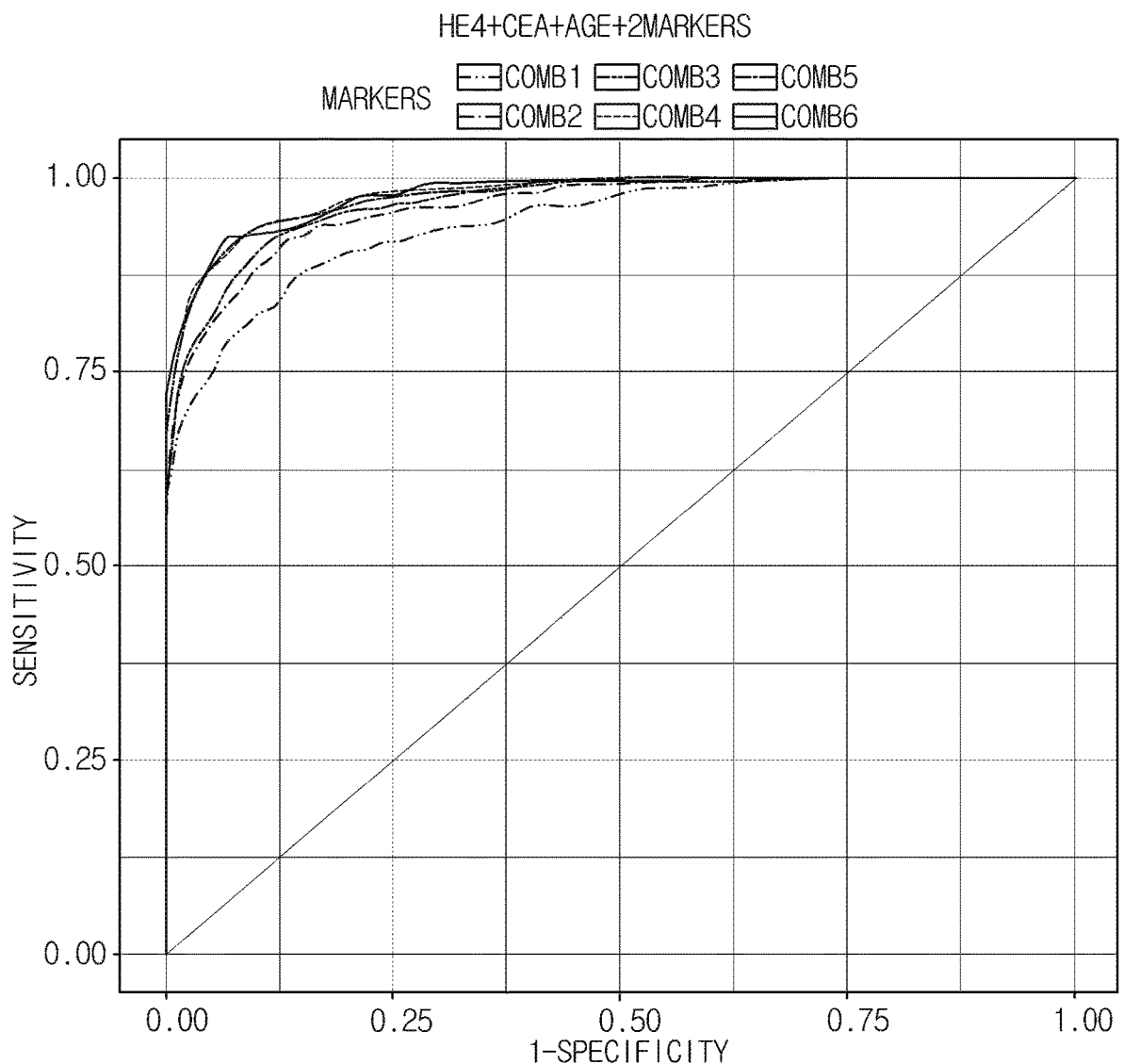

Ranges of the regression coefficients of the regression model confirmed with the 10-fold cross validation. As the above-mentioned exemplary logistic regression model was drawn from all the training data sets, the regression coefficients of the regression model were set to a single value, but the ranges of the regression coefficients of the individual biomarkers can be obtained by the 10-fold cross validation which draws the regression model repeatedly for nine tenths of the whole experimental group. The result is shown in FIG. 9 below.

TABLE 9

|  | Minimum Value | Maximum Value |
|---|---|---|
| HE4 (i.e., HE4 calibrated) | 2.779537 | 3.30755 |
| CEA | 1.182147 | 1.448989 |
| ApoA2 | −1.56861 | −1.35275 |
| RANTES | −2.69601 | −2.45476 |
| TTR | −1.76552 | −1.48475 |
| Svcam.1 | −1.95726 | −1.72294 |
| age | 1.130043 | 1.394296 |
| (intercept) | −0.83606 | −1.03448 |

Herein, the unit of the regression coefficients of the individual biomarkers is expressed inversely to, the unit of the experimental data values thereof. It is because result values, i.e., dependent variables, of the logistic regression model must be without units. As the unit of the experimental data of HE4 is log(pM), the unit of the regression coefficient of HE4 becomes $\{\log(pM)\}^{-1}$. In addition, because the unit of the experimental data of ApoA2 and TTR is log(mg/dL), the unit of the regression coefficient of the ApoA2 and the TTR, respectively, becomes $\{\log(mg/dL)\}^{-1}$. Since the unit of the experimental data of sVCAM-1, CEA, and RANTES is log(ng/mL), the unit of the regression coefficient of sVCAM-1, CEA, and RANTES, respectively, becomes $\{\log(ng/mL)\}^{-1}$. The range of the regression coefficient is exemplary, and is not limited to the logistic regression model in accordance with the present invention.

Evaluation of predictive performance by using experimental group of patients with SCLC. As the classifier was built only with normal persons and NSCLC patients, the inventors executed prediction to determine whether the patients with SCLC in the experimental group are lung cancer patients or not by using the classifier to confirm whether it produces the classification performance even for SCLC. Clearly, the experimental group must be diagnosed as the lung cancer patients. The result of the prediction is presented in Table 10 below.

TABLE 10

|  | Number of cases | sensitivity at cutoff = 0.3700928 |
|---|---|---|
| SCLC (Small Cell Lung Cancer) | 41 | 100% |

Given Table 10, the remarkable result can be identified that cancer was diagnosed in all of 41 subjects with the sensitivity level of 100%.

Comparison Between the Complex Biomarker Group in Accordance with the Present Invention and Other Complex Biomarker Groups.

Now also for said other complex biomarker groups utilizing individual biomarkers, the logistic regression model is used to derive the AUC. The result is shown in Table 11 below.

TABLE 11

| Index | MARKERS | | AUC | AUC rank |
|---|---|---|---|---|
| *Two markers among cancer-specific markers Cyfra21-1, CEA, and HE4 | | | | |
| 1 | Cyfra21-1 | CEA | 0.805 | 21 |
| 2 | Cyfra21-1 | HE4 | 0.894 | 18 |
| 3 | CEA | HE4 | 0.897 | 17 |

TABLE 11-continued

| Index | MARKERS | | | | | | AUC | AUC rank |
|---|---|---|---|---|---|---|---|---|
| \*Two markers among cancer-specific markers Cyfra21-1, CEA, and HE4 + age | | | | | | | | |
| 1 | age | Cyfra21-1 | CEA | | | | 0.824 | 20 |
| 2 | age | Cyfra21-1 | HE4 | | | | 0.894 | 19 |
| 3 | age | CEA | HE4 | | | | 0.898 | 16 |
| \*CEA, HE4 + 1 marker + age | | | | | | | | |
| 1 | age | CEA | HE4 | ApoA2 | | | 0.929 | 15 |
| 2 | age | CEA | HE4 | TTR | | | 0.931 | 14 |
| 3 | age | CEA | HE4 | sVCAM-1 | | | 0.931 | 13 |
| 4 | age | CEA | HE4 | RANTES | | | 0.959 | 10 |
| \*CEA, HE4 + 2 markers + age | | | | | | | | |
| 1 | age | CEA | HE4 | ApoA2 | TTR | | 0.939 | 12 |
| 2 | age | CEA | HE4 | ApoA2 | sVCAM-1 | | 0.957 | 11 |
| 3 | age | CEA | HE4 | TTR | sVCAM-1 | | 0.964 | 9 |
| 4 | age | CEA | HE4 | ApoA2 | RANTES | | 0.973 | 6 |
| 5 | age | CEA | HE4 | TTR | RANTES | | 0.974 | 5 |
| 6 | age | CEA | HE4 | sVCAM-1 | RANTES | | 0.973 | 7 |
| \*CEA, HE4 + 3 markers + age | | | | | | | | |
| 1 | age | CEA | HE4 | ApoA2 | TTR | sVCAM-1 | 0.969 | 8 |
| 2 | age | CEA | HE4 | ApoA2 | TTR | RANTES | 0.978 | 4 |
| 3 | age | CEA | HE4 | ApoA2 | sVCAM-1 | RANTES | 0.984 | 3 |
| 4 | age | CEA | HE4 | TTR | sVCAM-1 | RANTES | 0.986 | 2 |
| \*CEA, HE4 + 4 markers + age | | | | | | | | |
| 1 | Age | CEA | HE4 | ApoA2 | TTR | sVCAM-1 RANTES | 0.988 | 1 |

In Table 11, various combinations of biomarkers are represented in each row. In particular, data corresponding to the best combination of biomarkers in accordance with the present invention are provided in the bottom row. Herein, AUCrank means a ranking in order of AUC. In addition, one example embodiment of the ROC curves of the complex biomarker groups shown in Table 11 is illustrated more specifically in FIGS. 6 through 10.

Figure 6:
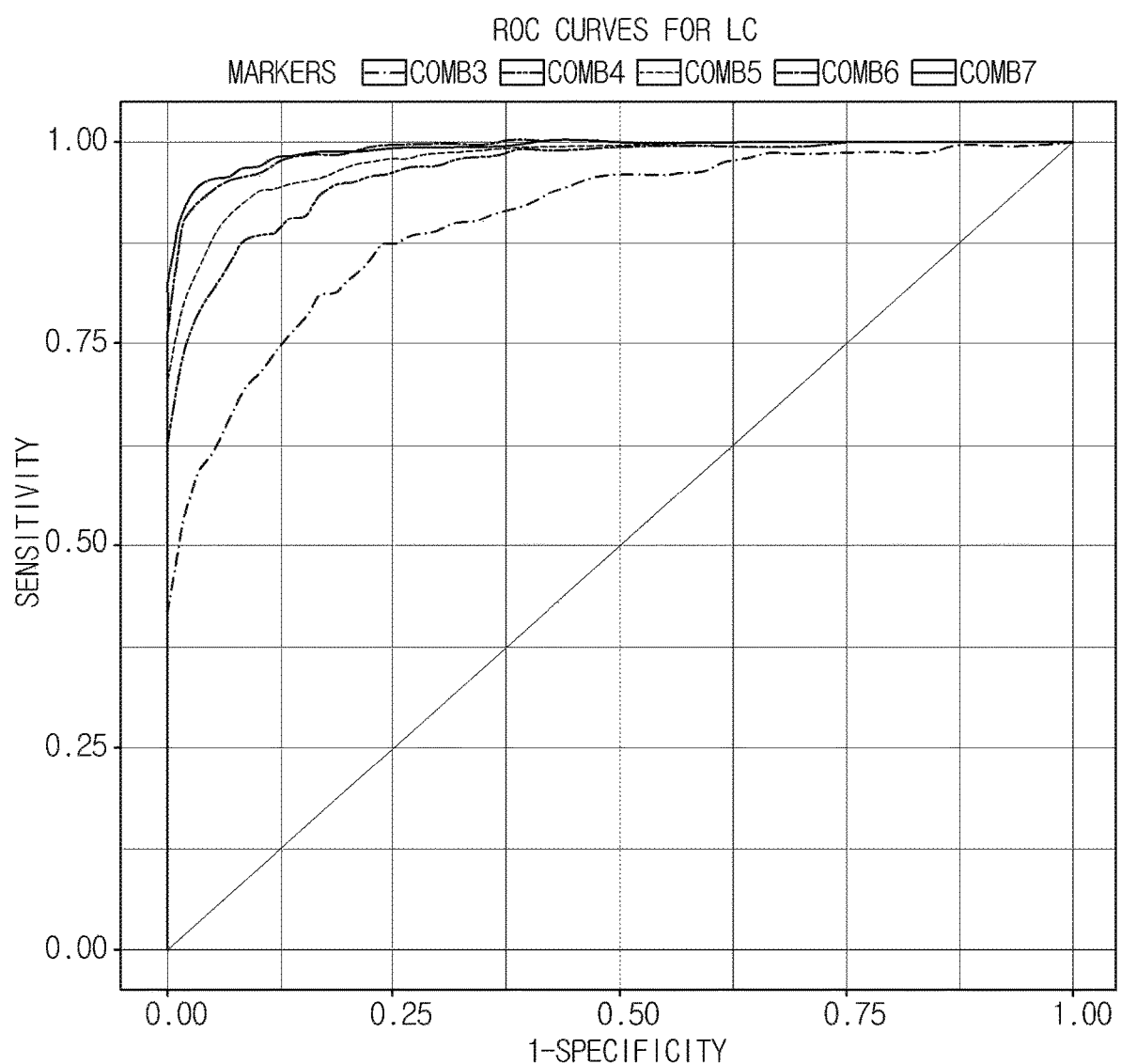
FIGS. 6 to 10 are graphs exemplarily illustrating ROC curves as indicators for evaluating various combinations of the biomarkers.

In FIG. 6, ROC curves were acquired by increasing the number of biomarkers added to complex biomarker groups containing HE4 and CEA. Herein, comb3 means an ROC curve acquired by using HE4 and CEA only; comb4 means an ROC curve acquired by adding RANTES to HE4 and CEA; comb5 means an ROC curve acquired by adding RANTES and TTR to HE4 and CEA; comb6 means an ROC curve acquired by adding RANTES, TTR and sVCAM-1 to HE4 and CEA; and comb7 means an ROC curve acquired by adding RANTES, TTR, sVCAM-1 and ApoA2 to HE4 and CEA. Herein, the factor of age is considered for the comb3 to the comb7. Among them in FIG. 6, the complex biomarker group including HE4, CEA, RANTES, TTR, sVCAM-1, ApoA2 as comb7 have the highest accuracy.

Next, in FIG. 7, ROC curves were acquired by using various combinations of two biomarkers. Herein, comb1 means an ROC curve acquired by using HE4 and CEA; comb2 means an ROC curve acquired by using CEA and Cyfra21-1; and comb3 means an ROC curve acquired by using HE4 and RANTES. All the combinations considered the factor of age together.

Figure 8:
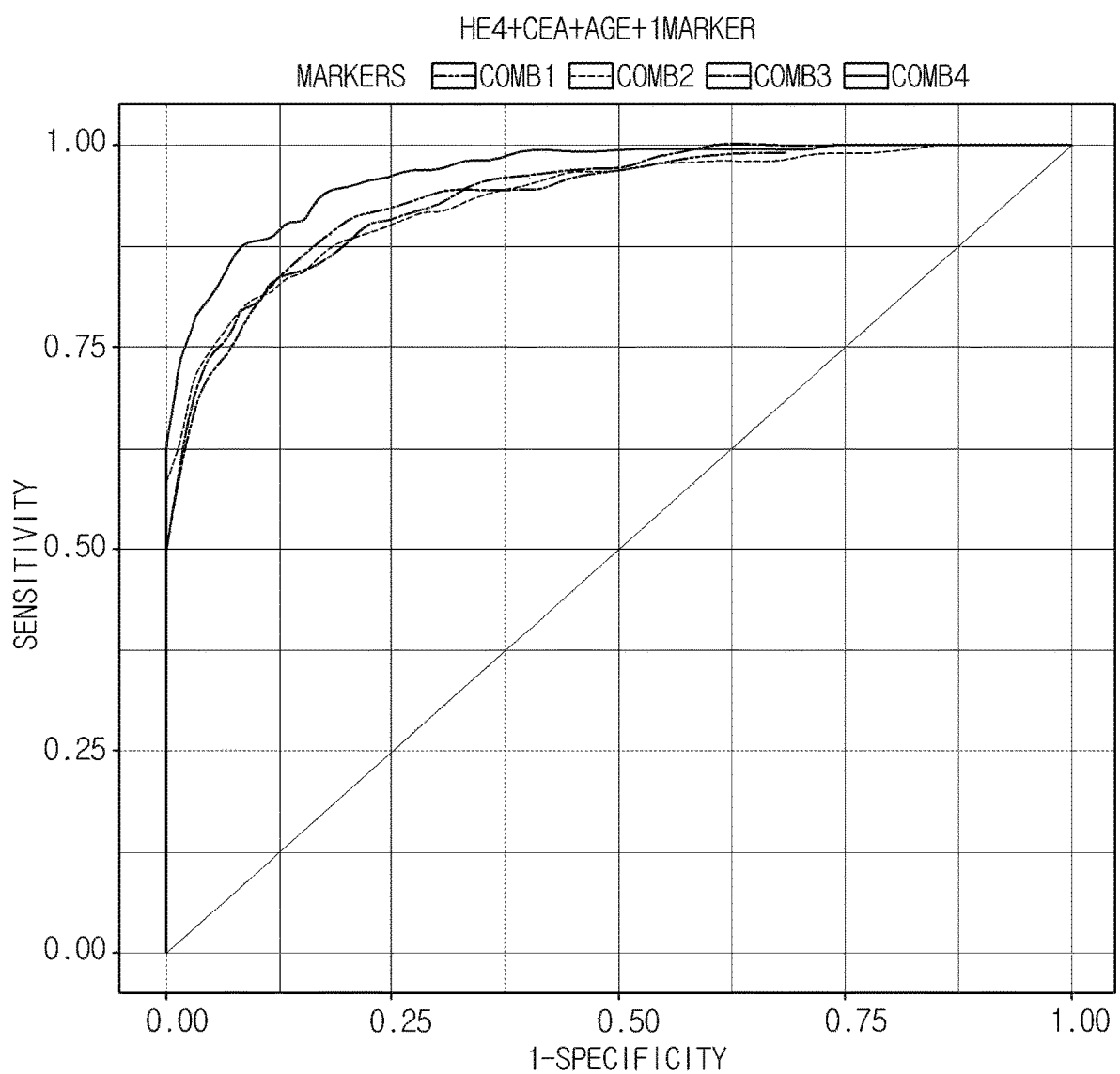

Besides, in FIG. 8, ROC curves were acquired by using combinations of HE4, CEA and one additional biomarker. Herein, comb1 means an ROC curve acquired by using a combination of HE4, CEA, and ApoA2; comb2 means an ROC curve acquired by using a combination of HE4, CEA, and TTR; comb3 means an ROC curve acquired by using a combination of HE4, CEA and sVCAM-1; and comb4 means an ROC curve acquired by using a combination of HE4, CEA, and RANTES. All the combinations considered the factor of age together. As indicated in FIG. 8 and Table 11, all the combinations showed higher accuracy compared to the combinations illustrated in FIG. 7. In particular, comb4 which includes all HE4, CEA, and RANTES had the highest accuracy.

In FIG. 9, ROC curves were acquired by using combinations of HE4, CEA and two additional biomarkers. Herein comb1 means an ROC curve acquired by using a combination of HE4, CEA, ApoA2, and TTR; comb2 means an ROC curve acquired by using a combination of HE4, CEA, ApoA2, and sVCAM-1; comb3 means an ROC curve acquired by using a combination of HE4, CEA, TTR, and sVCAM-1; comb4 means an ROC curve acquired by using a combination of HE4, CEA, ApoA2, and RANTES; comb5 means an ROC curve acquired by using a combination of HE4, CEA, TTR, and RANTES; and comb6 means an ROC curve acquired by using a combination of HE4, CEA, sVCAM-1, and RANTES. All the combinations considered the factor of age together. Compared to the combinations as graphed in FIG. 8, all the combinations in FIG. 9 and Table 11 have much higher accuracy.

Figure 10:
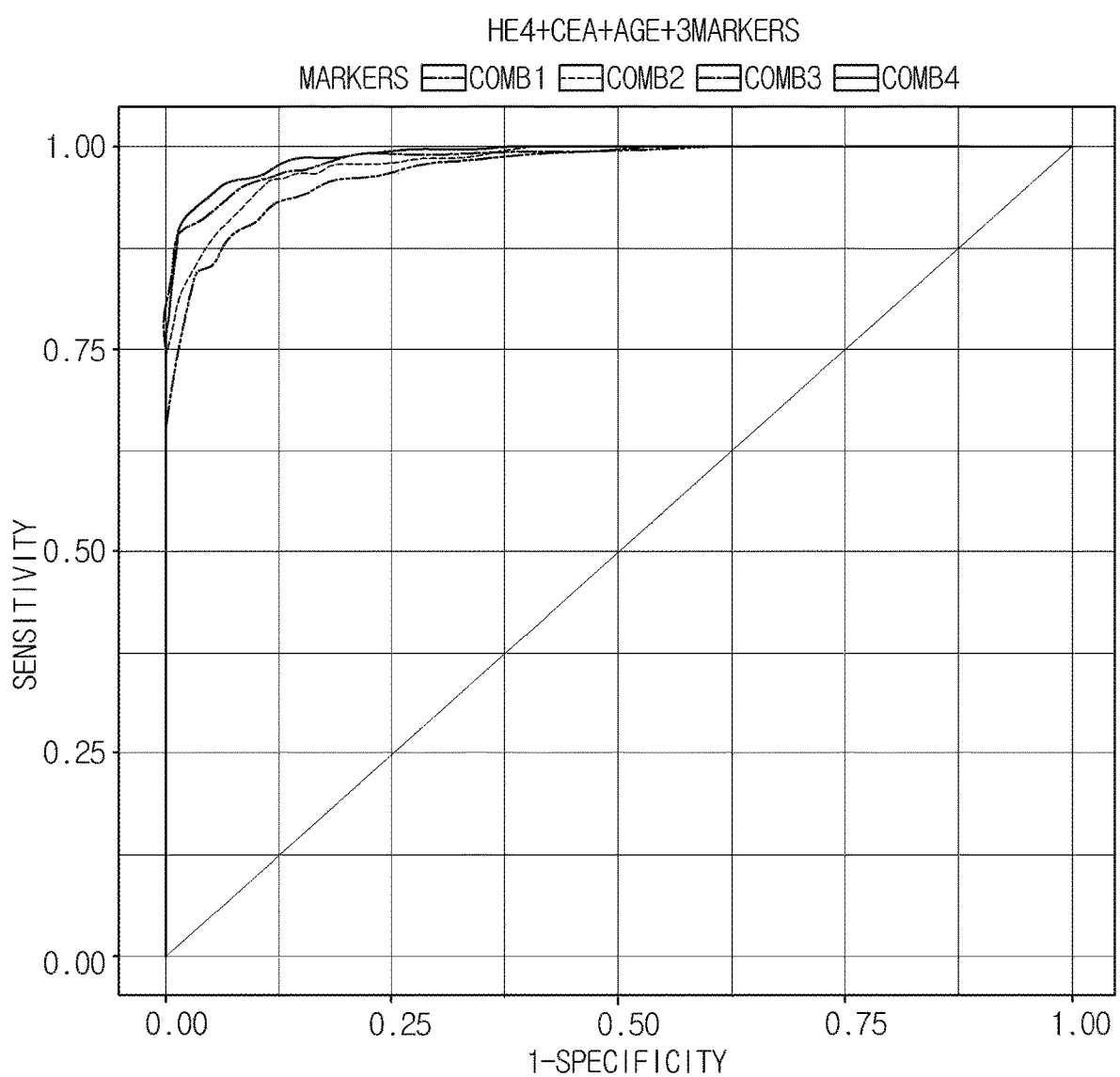

Finally, in FIG. 10, ROC curves were acquired by using combinations of HE4, CEA and three additional biomarkers. Herein, comb1 means an ROC curve acquired by using a combination of HE4, CEA, ApoA2, TTR, and sVCAM-1; comb2 means an ROC curve acquired by using a combination of HE4, CEA, ApoA2, TTR, and RANTES; comb3 means an ROC curve acquired by using a combination of HE4, CEA, ApoA2, sVCAM-1, and RANTES; comb4 means an ROC curve acquired by using a combination of HE4, CEA, TTR, sVCAM-1, and RANTES. All the combinations considered the factor of age together. All the combinations shown in FIG. 10 and Table 11 show far more excellent performance compared to combinations in FIG. 8 as mentioned above.

According to the result of the experiment of the present invention described above, it was found that the complex biomarker group consisting of HE4, CEA, RANTES, TTR, sVCAM-1, and ApoA2 shows the most excellent performance in determining whether lung cancer occurs, and that they functioned as highly accurate biomarkers with an AUC of 0.988. For example, lung cancer can be diagnosed very accurately by using the above-mentioned combination of the complex biomarker group in accordance with the present invention.

In accordance with the preferred embodiment of the present invention, the complex biomarker group is limited to the six individual biomarkers, but according to Table 11, the scope of effective complex biomarker groups for diagnosing lung cancer could be expanded to various complex biomarker groups including at least one of ApoA2, TTR, and sVCAM-1 with CEA, HE4, and RANTES as essential biomarkers. As shown in Table 11, among combinations comprised of four individual biomarkers, the performance (e.g., AUCranks of the 5th, 6th and 7th places) of combinations including CEA, HE4, and RANTES as essential biomarkers and one additional biomarker selected among ApoA2, TTR and sVCAM-1 is excellent compared to the performance (e.g., AUCranks of the 9th, 11th and 12th places) of other combinations of four individual biomarkers. Besides, even among combinations comprised of five individual biomarkers, the performance of combinations including CEA, HE4, and RANTES as essential biomarkers and two additional biomarkers selected among ApoA2, TTR, and sVCAM-1 is more excellent than that of other combinations of five individual biomarkers. Therefore, it could be easily understood by those skilled in the art that complex biomarker groups including CEA, HE4, RANTES and at least one of ApoA2, TTR, and sVCAM-1 may be useful for diagnosis of lung cancer in a subject in accordance with the present invention.

Besides, in accordance with the present invention, a lung cancer diagnostic kit is provided. In detail, the lung cancer diagnostic kit includes antibodies specifically binding to the individual biomarkers, i.e., CEA, HE4, ApoA2, TTR, sVCAM-1, and RANTES. Such a lung cancer diagnostic kit could be used for the purpose of not only determining whether lung cancer occurs or not but also even of monitoring or screening lung cancer.

As explained above, the antibodies included in the lung cancer diagnostic kit may include polyclonal antibodies, monoclonal antibodies, or fragments capable of binding to epitope, etc. Herein, the polyclonal antibodies can be acquired by using a conventional method of injecting one of the individual biomarkers to an animal and taking its blood thereby to acquire blood serum including antibodies.

Such polyclonal antibodies may be refined under any method well known in the field of the technology, and may be made from hosts of animal species including, but not limited to, goats, rabbits, sheep, monkeys, horses, pigs, cows, and dogs.

In addition, monoclonal antibodies can be acquired by using any technology for creating antibody molecules through the cultivation of continuous cell lines. Such a technology includes hybridoma technology, human B cell hybridoma technology, and EBV hybridoma technique (Kohler G et al., Nature 256:495-497, 1975; Kozbor D et al., J Immunol Methods 81:31-42, 1985; Cote R J et al., Proc Natl Acad Sci 80:2026-2030, 1983; and Cole S P et al., Mol Cell Biol 62:109-120, 1984) but it is not limited to these.

Besides, antibody fragments containing a part specifically binding to one of the individual biomarkers can be acquired. For example, F(ab') 2 antibody fragments can be produced by decomposing antibody molecules into pepsin. Fab fragments can be manufactured by reducing disulfide bridges of the F(ab') 2 antibody fragments but they are not limited to this. As an alternative, Fab expression libraries can be constructed to allow rapid and easy identification of monoclonal Fab fragments with the desired specificity (see Huse W D et al., Science 254: 1275-1281, 1989).

The antibodies can be bound to solid substrates to facilitate subsequent steps such as cleansing, separation of complex bodies, etc. The solid substrates include, for example, synthetic resins, nitrocellulose, glass substrates, metal substrates, glass fibers, paramagnetic beads, microspheres, microbeads, etc. In addition, the synthetic resins include polyester, polyvinyl chloride, polystyrene, polypropylene, PVDF, nylon, etc. In the specific example embodiment of the present invention, to combine antibodies specifically binding to proteins with the solid substrates, microspheres were suspended; moved to a microtube to remove the supernatant by centrifugation; re-suspended; processed with regard to N-hydroxy-sulfosuccinimide and 1-ethyl-3-(3-dimethylaminopropyl)-carbodiimide hydrochloride in order; and cleaned and kept with the supernatant removed by centrifugation. In addition, before the specimen acquired from a subject contacts an antibody that can specifically bind to one of the individual biomarkers in accordance with the present invention which is combined with the solid substrates, the specimen may be diluted to an appropriate degree.

The kit in accordance with the present invention may additionally include antibodies for detection specifically binding to the biomarkers. The antibodies for detection may be conjugates labeled as detectors such as chromogenic enzymes, fluorescent materials, radioisotopes, or colloids and more preferably, they may be primary antibodies that can specifically bind to the biomarkers. For example, the chromogenic enzymes may be peroxidase, alkaline phosphatase, or acid phosphatase {for example, horseradish peroxidase} and the fluorescent materials may be fluorescein carboxylic acid (FCA), fluorescein isothiocyanate (FITC), fluorescein thiourea (FTH), 7-acetoxy-coumarin-3-yl, fluorescein-5-yl, fluorescein-6-yl, 2',7'-dichlorofluorescein-5-yl, 2',7'-dichlorofluorescein-6-yl, dihydrotetramethylrosamin-4-yl, tetramethylrodamin-5-yl, tetramethylrodamin-6-yl, 4,4-difluoro-5,7-dimethyl-4-bora-3a,4a-diaza-s-indacene-3-ethyl, or 4,4-difluoro-5,7-diphenyl-4-bora-3a,4a-diaza-s-indacene-3-ethyl, Cy3, Cy5, poly L-lysine-fluorescein isothiocyanate (FITC), rhodamine-B-isothiocyanate (RITC), rhodamine, phycoerythrin (PE), etc.

In addition, the kits in accordance with the present invention may additionally include (1) antibodies for detection that specifically bind to the biomarkers and (2) ligands that may specifically bind to the antibodies for detection. The ligands include secondary antibodies specifically binding to protein A or the antibodies for detection, etc. Besides, the ligands may be conjugates labeled as detectors such as chromogenic enzymes, fluorescent materials, radioisotopes, or colloids. It is desirable to use the primary antibodies after a process of biotinylation or digoxigenin, but the methods for processing the antibodies for detection are not limited to this. Besides, it is desirable to use streptavidin, abidin, etc. as the ligands to be combined with the antibodies for detection but it is not limited to this. In the specific example embodiment of the present invention, streptavidin attaching a fluorescent material as a detector was used as the ligand and the biotinylated antibody for detection was used for the ligand.

In the present invention, the lung cancer diagnostic kit can diagnose, monitor and screen lung cancer by measuring amount of the antibodies for detection which have been processed with the antibodies and the biomarker complex. Otherwise, after the antibodies for detection and the ligand were processed with the antibodies and the biomarker complex in consecutive order, the lung cancer diagnostic kit can diagnose, monitor and screen lung cancer by measuring the amount of the antibodies for detection. In accordance with the preferred example embodiment of the present invention, it can measure amount of the biomarkers by placing the antibodies for detection with a combination of the antibodies and biomarker complex in a constant temperature, cleaning them, and measuring the antibodies for detection. The measurement of amount of the antibodies for detection or the detection of the existence could be made through fluorescence, luminescence, chemiluminescence, absorbency, reflection or penetration.

In addition, it is desirable to use a high throughput screening (HTS) system as a method for measuring the antibodies for detection or amount of the ligand. Herein, fluorescence method conducted by detecting fluorescence with fluorescent material being attached as a detector, a radiographic method by detecting radiation with radioactive isotope being attached as a detector; a surface plasmon resonance (SPR) method for measuring a change in plasmon resonance in real time without labeling of the detector or a surface plasmon resonance imaging (SPRI) method visualizing SPR may be used, but they are not limited to these.

For example, the binding degree of the antibodies may be identified by the fluorescent method which is a method for labeling the antibodies for detection with fluorescent material and spotting them with a fluorescence scanning program. It is desirable to select one of Cy3, Cy5, poly L-lysine-fluorescein isothiocyanate (FITC), rhodamine-B-isothiocyanate (RITC), rhodamine, and Phycoerythrin (PE) as the fluorescent material, but it is not limited to these. Contrary to the fluorescent method, the SPR system can analyze the binding degree of the antibodies in real time without a necessity to label a specimen with a fluorescent material but it has a drawback in that it is not possible to analyze specimens simultaneously. In case of the SPRI, it is possible to analyze specimens simultaneously by using a fine alignment method, but it has a drawback in that sensitiveness of the detection is low.

Besides, the lung cancer diagnostic kit in accordance with the present invention may additionally include a cleaning solution or an eluent which can remove substrates that color reacts with enzymes, non-binding proteins, etc. thus retaining bound biomarkers. The specimens used for analysis include biological specimens such as blood serum, urine, tear, and saliva that can show disease-specific poplypeptide different from that of a normal state. Preferably, specimens are biological fluid specimens, e.g., blood, blood serum, and plasma and more preferably, blood serum. The specimens can be prepared to increase detection sensitivity of the biomarkers. For example, the blood serum specimens acquired from patients can be pre-processed by using methods including anion-exchange chromatography, affinity chromatography, size exclusion chromatography, liquid chromatography, sequential extraction or gel electrophoresis, but such methods are not limited to these.

As another example embodiment, the lung cancer diagnostic kit in accordance with the present invention may include least six receptor sites; and six or more antibodies that are placed on at least six receptor sites respectively and are specifically binding to pre-set individual biomarkers. Herein, the six or more antibodies include antibodies specifically binding to the individual biomarkers CEA, HE4, ApoA2, TTR, sVCAM-1 and RANTES, respectively.

In addition, the present invention provides a biochip where biological molecules capable of specifically binding to the above-mentioned-individual biomarkers are integrated in a solid substrate. The biochip in accordance with the present invention may include an antibody capable of specifically binding to any of the individual biomarkers or a combination of antibodies specifically binding to two or more individual biomarkers.

The biological molecules are selected from low-molecular-weight compounds, ligands, aptamers, peptide, polypeptide, specifically binding proteins, high-molecular-weight compounds, antibodies, etc. and any materials capable of specifically binding to the proteins may be used as such biological molecules. It is desirable to use an antibody or an aptamer, but they are not limited to these.

As the antibody, it is possible to use a polyclonal antibody or a monoclonal antibody, but it is more desirable to use the monoclonal antibody. The antibody specifically binding to one of the proteins can be manufactured in a method disclosed to those skilled in the art and a commercially well-known antibody also can be purchased for use. The antibody may be produced by injecting a protein as an immunogen to an external host according to an existing method known to those skilled in the art. The external host includes a mammal such as mice, rats, sheep, and rabbits. The immunogen is injected intramuscularly, intraperitoneally, or hypodermically and it can be administered with an adjuvant generally to increase antigenicity. It is possible to draw blood regularly from the external host to collect blood serum showing specificity to a created potency and an antigen, and then separate the antibody from the blood serum.

Besides, a solid substrate of the biochip in accordance with the present invention may be selected from plastic, glass, metal and silicon and more desirably, it would be possible to be chemically processed or be combined with a linker molecule to attach the antibody to its surface but it is not limited to this. The biochip in accordance with the present invention may diagnose, monitor, and screen lung cancer easily and accurately.

An active group coated on the substrate of the biochip plays a role in combining the substance and it can be selected among amine group, aldehyde group, carboxyl group, and thiol group. All active groups known to those skilled in the art as active groups that can combine protein molecules to the substrate can be used, but they are not limited to these.

Besides, in accordance with the present invention, a method for diagnosing lung cancer in a subject by using the above-mentioned complex biomarker group is provided. The method includes steps of: (a) a computing system (1) acquiring a model for diagnosing lung cancer, wherein the model is established by using (i) expression level data by individual biomarkers from the complex biomarker group measured from biological specimens of a sample consisting of lung cancer patients and people without lung cancer or their processed data of the sample or (ii) the expression level data by the individual biomarkers or their processed data and ages of the sample and then (2) acquiring expression level data by the individual biomarkers measured from a biological specimen of the subject or their processed data or the expression level data by the individual biomarkers or their processed data and age of the subject; and (b) the computing system determining whether lung cancer is detected in the subject by using the acquired data of the subject by referring to the model. In other words, the model for diagnosing lung cancer can treat ages of the persons belonging to the sample and the measured data of the sample as independent variables.

In one example embodiment, the model for diagnosing lung cancer may be the logistic regression model as explained above. Besides, in accordance with one example embodiment, the preprocess at the step of (b) may include log (base 10) transformation of the expression level data, partially at least.

In accordance with the present invention, even a computing system for performing the aforementioned method is also provided.

Figure 11:
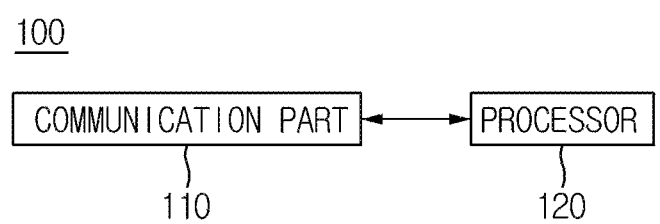
FIG. 11 is a conceptual diagram roughly depicting a configuration of a computing system for diagnosing lung cancer in a subject by using the complex biomarker group selected in accordance with the present invention.

FIG. 11 is a conceptual diagram roughly depicting a configuration of a computing system 100 that uses the complex biomarker group to detect lung cancer. By referring to FIG. 11, the computing system 100, a communication part 110 and a processor 120 as hardware components are illustrated.

Herein, the communication part 110 acquires a model for diagnosing lung cancer, wherein the model is established by using (1-i) expression level data by the individual biomarkers measured from biological specimens of a sample consisting of lung cancer patients and people without lung cancer or their processed data of the sample or (1-ii) the expression level data by the individual biomarkers or their processed data and ages of the sample, and then (2) acquires (2-i) expression level data by the individual biomarkers measured from a biological specimen of the subject or their processed data or (2-ii) the expression level data by the individual biomarkers or their processed data and age of the subject.

Moreover, the processor 120 preprocesses the expression level data of the subject by individual biomarkers and determines whether lung cancer occurs in the subject by using the processed and measured data of the subject or the measured data and age of the subject by referring to the model for diagnosing lung cancer.

As such, the computing system 100 in accordance with the present invention performs the method.

Based on the explanation on the example embodiment, those skilled in the art can clearly understand that the present invention can be executed through a variety of embodiments. As one example embodiment, the logistic regression model was used as a method for determining lung cancer in the present specification but any statistical model that explains binary dependent variables could be used. The part which deals with such statistical model can be implemented in a shape of program commands that can be performed through a variety of computer components. To deal with such statistical models in the present specification, R Statistical Package was used, but those skilled in the art would understand that any software such as SPSS, SAS, Mathematica or programming language capable of implementing such a statistical method that can perform operations required to construct the logistic regression model is available. They can be implemented in a form of executable program commands through a variety of computer means recordable to computer readable media. The computer readable media may include solely or in combination, program commands, data files, and data structures. The program commands recorded to the media may be components specially designed for the present invention or may be usable to a skilled person in a field of computer software. Computer readable record media include magnetic media such as hard disk, floppy disk, and magnetic tape, optical media such as CD-ROM and DVD, magneto-optical media such as floptical disk and hardware devices such as ROM, RAM, and flash memory specially designed to store and carry out programs. Program commands include not only a machine language code made by a compiler but also a high-level code that can be used by an interpreter etc., which is executed by a computer. The aforementioned hardware device can work as one or more software modules to perform the action of the present invention and vice versa. The hardware device may be combined with a memory device such as ROM or RAM to store the program commands and may include a processor such as CPU or GPU to execute commands stored in the memory and also a communication part which can receive or send signals from or to external devices. In addition, the hardware device may include a keyboard, a mouse, and any other external input device to receive commands prepared by developers.

Besides, in the aforementioned example embodiment, HE4, CEA, Cyfra21-1, RANTES, TTR, sVCAM-1, and ApoA2 were used as required individual biomarkers, but it would be understood by those skilled in the art that there are other individual biomarkers in addition to them. Anything that can be used with the individual biomarkers to improve the performance of the logistic regression model could be included, some of which may have been widely used so far in connection with the diagnosis of tumor in oncology, as a technical field where the present invention belongs, or is found to be connected with tumor. In the present specification, only protein markers as individual biomarkers were exemplarily used, but individual biomarkers available in addition to the required individual biomarkers are not limited to these. Biomarkers could include a variety of genetic markers, e.g., RNA, DNA markers, known in relation to the diagnosis of tumor, or quantifying other organic or inorganic substances, etc.

The present invention has an effect of organizing the selected biomarkers to diagnose lung cancer with the higher abilities compared to the existing complex biomarker groups.

The present invention also has an effect of increasing effectiveness of the lung cancer diagnostic kit and the method for diagnosing lung cancer by using the kit.

Besides, the present invention has an effect of increasing the survival rates of lung cancer patients through the effective diagnosis and allowing the treatment method to be changed according to the result of monitoring the reactions of the patients to treatment.

As seen above, the present invention has been explained by specific matters such as detailed components, limited embodiments, and drawings. While the invention has been shown and described with respect to the preferred embodiments, it, however, will be understood by those skilled in the art that various changes and modification may be made without departing from the spirit and scope of the invention as defined in the following claims.

Accordingly, the thought of the present invention must not be confined to the explained embodiments, and the following patent claims as well as everything including variants equal or equivalent to the patent claims pertain to the category of the thought of the present invention.

What is claimed is:

1. A method for diagnosing and treating lung cancer in a specific subject comprising steps of:
(a) establishing, using a computing system, a model M for diagnosing lung cancer by using (i) expression level data ($B_{ki}$) by the individual biomarkers the complex biomarker group, the individual biomarkers consisting of CEA, HE4, ApoA2, TTR, sVCAM-1 and RANTES, measured from biological specimens of a subject, group consisting of lung cancer patients and people without lung cancer (where k is an index for the individual biomarkers and i is an index for the individual biological specimens) and (ii) ages (age$_i$) of the subject group (where age$_i$ is the age of each individual of the subject group), wherein the model M for diagnosing lung cancer is a two-class classifier drawn by using the B$_{ki}$, and the age$_i$, and wherein the model M is a logistic regression model that follows a model equation:

$$\ln\left(\frac{P_i}{1-P_i}\right) = \alpha + \beta_1 B_{1i} + \beta_2 B_{2i} + \ldots + \beta_6 B_{6i} + \beta_7(\text{age}_i) + \epsilon_i$$

$$P_i = P(y_i = 1)$$

where $\alpha, \beta_1, \ldots, \beta_7$ indicate regression coefficients, and $\epsilon_i$ indicates a residual value;

(b) contacting a biological specimen from the specific subject with at least six antibodies placed on at least six receptor sites, respectively, wherein each of the at least six antibodies is specifically binding to a respective one of the individual biomarkers of the complex biomarker group;

(c) acquiring (i) expression level data by the Individual biomarkers measured from the biological specimen of the specific subject (B$_k$) and age (age) of the specific subject;

(d) diagnosing the specific subject with lung cancer using the expression level data and the age of the specific subject acquired in step (c) by referring to the model M; and (e) administering a lung cancer treatment to the diagnosed subject.

2. The method of claim 1, wherein the individual biomarkers in the complex biomarker group are selected by performing steps of:

(a1) a second computing system acquiring (i) expression level data of individual biomarkers x$_n$ belonging to a first biomarker set S$_1$ from a subject s belonging to a second sample or their processed data x$_{ns}$ or the processed data x$_{ns}$, and age data x$_{age,s}$ of the second sample and (ii) data y$_s$ on whether lung cancer has been detected, wherein the first biomarker set S$_1$ further includes additional individual biomarkers in addition to CEA, HE4, ApoA2, TTR, sVCAM-1 and RANTES;

(a2) the second computing system calculating a p-value for the individual biomarkers belonging to the first biomarker set S$_1$ by performing at least one of (i) a chi-square test under a null hypothesis that the y$_s$ and the x$_{ns}$ are independent with each other and (ii) a Student's t-test under a null hypothesis that a true value of difference is 0 between an average of x$_{ns}$ subjects who are diagnosed with lung cancer and that of subjects who are not;

(a3) the second computing system acquiring a second biomarker set S$_2$ consisting of individual biomarkers with p-values smaller than a pre-set significance level by comparing the respective p-values calculated at the step of (a2) with the pre-set significance level;

(a4) the second computing system obtaining estimation values $\widehat{x_m}$ of individual biomarkers x$_m$ belonging to the second biomarker set S$_2$ respectively for the subjects who are diagnosed with lung cancer arid the subjects who are not through a regression model equation:

$$\widehat{x_m} = \widehat{\beta_0} + \Sigma_{xj \in S_m}(\widehat{\beta_j} \times x_{js}) + \widehat{\beta_{age}} \times x_{age,s}$$

where Sm'=S$_2$−{x$_m$} and $\beta_{age}$ and $\beta_j$ indicate regression coefficients;

(a5) the second computing system obtaining residual values x$_m$−$\widehat{x_m}$ regarding the individual biomarkers x$_m$ respectively for the subjects who are diagnosed with lung cancer and the subjects who are not;

(a6) the second computing system calculating p-values for the individual biomarkers belonging to the S$_2$ by performing a Student's t-test under a null hypothesis that a true value of difference is 0 between an average of the residual values of the subjects who are diagnosed with lung cancer and that of the subjects who are not; and (a7) the second computing system selecting individual biomarkers with p-values smaller than a pre-set significance level by comparing the p-values calculated at the step of (a6) and the pre-set significance level.

3. A method for diagnosing and treating lung cancer in a specific subject, the method comprising:

(a) obtaining a biological sample from a human subject;

(b) detecting the expression level of a carcinoembryonic antigen (CEA), human epididymis protein 4 (HE4), apolipoprotein A-II (ApoA2), transthyretin (TTR), soluble vascular cell adhesion molecule-1 (sVCAM-1), and RANTES {regulated on activation, normal T cell expressed and secreted; Chemokine (C-C motif) ligand 5} in the biological sample by contacting the sample with at least one CEA-binding antibody, at least one HE4-binding antibody, at least one ApoA2-binding antibody, at least one ITR-binding antibody, at least one sVCAM-1-binding antibody, and at least one RANTES-binding antibody and detecting binding between CEA and the at least one CEA-binding antibody, HE4 and the at least one HE4-binding antibody, ApoA2 and the at least one ApoA2-binding antibody, TTR and the at least one TTR-binding antibody, sVCAM-1 and the at least one sVCAM-1-binding antibody, and RANTES and the at least one RANTES-binding antibody;

(c) diagnosing the subject with lung cancer using the expression level data (B$_{ki}$) of CEA, HE4, ApoA2, TTR, sVCAM-1, and RANTES in a model M, wherein the model M is established using (i) the expression level of CEA, HE4, ApoA2, TTR, sVCAM-1, and RANTES as measured from biological specimens of a subject group consisting of lung cancer patient and individuals without lung cancer (where k is an index for the individual biomarkers and i is an index for the individual biological specimens) and ages (age$_i$) of the subject group (where age$_i$ is the age of each individual of the subject group), wherein the model M for diagnosing lung cancer is a logistic regression model that follows a model equation;

$$\ln\left(\frac{P_i}{1-P_i}\right) = \alpha + \beta_1 B_{1i} + \beta_2 B_{2i} + \ldots + \beta_6 B_{6i} + \beta_7(\text{age}_i) + \epsilon_i$$

$$P_i = P(y_i = 1)$$

where $\alpha, \beta_1, \ldots, \beta_7$ indicate regression coefficients, and $\epsilon_i$ indicates a residual value; and (d) administering a lung cancer treatment to the diagnosed subject.

4. The method of claim 3, wherein the at least one CEA-binding antibody, at least one HE4-binding antibody, at least one ApoA2-binding antibody, at least one TTR-binding antibody, at least one sVCAM-1-binding antibody, and at least one RANTES-binding antibody are each bound to a solid substrate, and the method further includes a step of providing the solid substrate.

* * * * *